United States Patent
Khodagholy et al.

(10) Patent No.: US 12,201,741 B2
(45) Date of Patent: Jan. 21, 2025

(54) COMPOSITES AND DEVICES FOR INTERFACING ELECTRONICS TO BIOLOGICAL TISSUE

(71) Applicant: The Trustees of Columbia University in the City of New York, New York, NY (US)

(72) Inventors: Dion Khodagholy, New York, NY (US); Patricia Jastrzebska-Perfect, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1108 days.

(21) Appl. No.: 17/022,004

(22) Filed: Sep. 15, 2020

(65) Prior Publication Data

US 2021/0077656 A1    Mar. 18, 2021

Related U.S. Application Data

(60) Provisional application No. 62/900,633, filed on Sep. 15, 2019.

(51) Int. Cl.
| | |
|---|---|
| A61L 24/00 | (2006.01) |
| A61B 5/25 | (2021.01) |
| A61B 5/259 | (2021.01) |
| A61L 24/08 | (2006.01) |
| C08G 61/12 | (2006.01) |
| C08L 5/00 | (2006.01) |
| C08L 5/08 | (2006.01) |
| C08L 81/02 | (2006.01) |
| C09D 165/00 | (2006.01) |
| C09J 105/00 | (2006.01) |

(52) U.S. Cl.
CPC .......... *A61L 24/0094* (2013.01); *A61B 5/259* (2021.01); *A61L 24/001* (2013.01); *A61L 24/08* (2013.01); *C08G 61/126* (2013.01); *C08L 5/00* (2013.01); *C08L 5/08* (2013.01); *C08L 81/02* (2013.01); *C09D 165/00* (2013.01); *C09J 105/00* (2013.01); *A61B 5/25* (2021.01); *A61B 2562/0217* (2017.08); *C08G 2261/11* (2013.01); *C08G 2261/1424* (2013.01); *C08G 2261/3223* (2013.01); *C08G 2261/794* (2013.01); *C08L 2203/02* (2013.01)

(58) Field of Classification Search
CPC .... A61L 24/0094; A61L 24/08; A61L 24/001; A61B 5/25; A61B 2562/0217; A61B 5/259; C08G 61/126; C08G 2261/11; C08G 2261/1424; C08G 2261/3223; C08G 2261/794; C08L 5/00; C08L 81/02; C08L 5/08; C08L 2203/02; C09D 165/00; C09J 105/00
See application file for complete search history.

(56) References Cited

U.S. PATENT DOCUMENTS

| | | |
|---|---|---|
| 5,200,051 A | 4/1993 | Cozzette et al. |
| 6,577,893 B1 | 6/2003 | Besson et al. |
| 7,357,810 B2 | 4/2008 | Koyfman et al. |
| 7,952,090 B2 | 5/2011 | Kugler |
| 7,967,839 B2 | 6/2011 | Flock et al. |
| 8,137,524 B2 | 3/2012 | Berggren et al. |
| 8,398,680 B2 | 3/2013 | Sauer et al. |
| 8,777,988 B2 | 7/2014 | Leung et al. |
| 9,178,170 B2 | 11/2015 | Yan et al. |
| 9,201,039 B2 | 12/2015 | Hanko et al. |
| 2008/0283833 A1 | 11/2008 | Kim et al. |
| 2009/0163951 A1 | 6/2009 | Simmons et al. |
| 2009/0286097 A1 | 11/2009 | Yang et al. |
| 2009/0321721 A1 | 12/2009 | Malenfant et al. |

(Continued)

FOREIGN PATENT DOCUMENTS

| | | |
|---|---|---|
| CN | 106770515 | 5/2017 |
| KR | 101713240 | 3/2017 |

(Continued)

OTHER PUBLICATIONS

Abidian, M.R., et al., "Conducting-Polymer Nanotubes Improve Electrical Properties, Mechanical Adhesion, Neural Attachment, and Neurite Outgrowth of Neural Electrodes", In Small, vol. 6, No. 3, Jan. 2010, pp. 421-429.

Adair, E. R., et al., "Biological effects of radiofrequency/microwave radiation", In IEEE Transactions Microwave Theory Technology, vol. 50, Mar. 2002, pp. 953-962.

Adam, C., "Fibrin Sutures for Non-Scarring Wound Closure", Vitathreads, LLC, NIH Grant R43GM112344, last accessed Nov. 13, 2023, pp. 1-5, available at: https://reporter.nih.gov/search/CcM5mSDoAEGnsxLD5JYH1w/project-details/8834658.

(Continued)

*Primary Examiner* — Patrick D Niland
(74) *Attorney, Agent, or Firm* — Byrne Poh LLP

(57) ABSTRACT

Composites, are provided, the composites comprising: mixed conducting particles; and an ion conducting scaffolding matrix. In some embodiments, the mixed conducting particles are made from poly(3,4-ethylenedioxythiophene)-poly(styrenesulfonate). In some embodiments, the ion conducting scaffolding matrix includes a chitosan (CS)-based polymer. In some embodiments, devices are provided, the devices comprising: a composite comprising mixed conducting particles and an ion conducting scaffolding matrix; and three electrodes, wherein: each of the three electrodes is in contact with the composite; a first pair of the three electrodes are on opposite sides of the composite and are a distance h apart; a second pair of the three electrodes are on a same side of the composite and are a distance d1 apart; a particle size of the mixed conducting particles is between h and d1; a mean-free-path of the mixed conducting particles is less than d1; and the composite behaves like an anisotropic conductor.

15 Claims, 32 Drawing Sheets

(56) References Cited

U.S. PATENT DOCUMENTS

| | | |
|---|---|---|
| 2010/0032661 A1 | 2/2010 | Osterbacka et al. |
| 2015/0115227 A1 | 4/2015 | Yan et al. |
| 2017/0174872 A1* | 6/2017 | Zhang .................. C08L 5/04 |
| 2018/0226256 A1 | 8/2018 | Li et al. |
| 2018/0362342 A1 | 12/2018 | Wu et al. |

FOREIGN PATENT DOCUMENTS

| | | |
|---|---|---|
| WO | WO 2003046540 | 11/2002 |
| WO | WO 2005037098 | 10/2004 |

OTHER PUBLICATIONS

Ahmadi, N., et al., "Towards a Distributed, Chronically-Implantable Neural Interface", In 2019 9th International IEEE/EMBS Conference on Neural Engineering, San Francisco, CA, Mar. 20-23, 2019, pp. 719-724.

Alcaraz, J. P., et al., "Tackling the Concept of Symbiotic Implantable Medical Devices with Nanobiotechnologies", In Biotechnology Journal, vol. 13, No. 12, Dec. 10, 2018, pp. 1-12.

Alivisatos, A. P., et al., "Neuroscience: The Brain Activity Map", In Science, vol. 339, No. 6125, Mar. 15, 2013, pp. 1284-1285.

Ando, H., et al., "Wireless Multichannel Neural Recording with a 128-Mbps UWB Transmitter for an Implantable Brain-Machine Interfaces", In IEEE Transactions on Biomedical Circuits and Systems, vol. 10, No. 6, Feb. 2016, pp. 1068-1078.

Arias, A.C., et al., "Materials and Applications for Large Area Electronics: Solution-based approaches", In Chemical Reviews, vol. 110, No. 1, Jan. 2010, pp. 3-24.

Benninger, D., et al., "Deep Brain Stimulation", In Therapeutische Umschau, Revue Therapeutique, vol. 75, No. 7, Jan. 2018, pp. 425-431.

Berggren, M. and Richter-Dahlfors, A., "Organic Bioelectronics", In Advanced Materials, Sep. 25, 2007, pp. 3201-3213.

Berggren, M., et al., "Organic Materials for Printed Electronics", In Nature Materials, vol. 6, Jan. 1, 2007, pp. 1-3.

Bernards, D.A. and Malliaras, G.G., "Steady-State and Transient Behavior of Organic Electrochemical Transistors", In Advanced Functional Materials, vol. 17, No. 17, Nov. 2007, pp. 3538-3544.

Biederman, W., et al., "A Fully-Integrated, Miniaturized (0.125 mm2) 10.5 µW Wireless Neural Sensor", In IEEE Journal of Solid-State Circuits, vol. 48, No. 4, Mar. 2013, pp. 960-970.

Boccaccini, A. R., et al., "Composite Surgical Sutures with Bioactive Glass Coating", In Journal of Biomedical Materials Research: Part B, Applied Biomaterials, vol. 67, No. 1, Oct. 15, 2003, pp. 618-626.

Bolin, M.H., et al., "Active Control of Epithelial Cell-Density Gradients Grown Along the Channel of an Organic Electrochemical Transistor", In Advanced Materials, vol. 21, No. 43, Nov. 20, 2009, pp. 4379-4382.

Borton, D.A., et al., "An Implantable Wireless Neural Interface for Recording Cortical Circuit Dynamics in Moving Primates", In Journal of Neural Engineering, vol. 10, No. 2, Feb. 2013, pp. 1-25.

Braga, D., et al., "High-Transconductance Organic Thin-Film Electrochemical Transistors for Driving Low-Voltage Red-Green-Blue Active Matrix Organic Light-Emitting Devices", In Advanced Functional Materials, vol. 22, No. 8, Apr. 24, 2012, pp. 1623-1631.

Buzsaki, G. and Draguhn, A., "Neural Oscillations in Cortical Networks", In Science, vol. 304, No. 5679, Jun. 25, 2004, pp. 1926-1929.

Buzsaki, G., "Hippocampal Sharp Wave-Ripple: A cognitive biomarker for episodic memory and planning", In Hippocampus, vol. 25, No. 10, Jul. 2015, pp. 1073-1188.

Buzsáki, G., "Large-Scale Recording of Neuronal Ensembles", In Nature Neuroscience vol. 7, No. 5, Apr. 27, 2004, pp. 446-451.

Buzsáki, G., et al. "Tools for Probing Local Circuits: High-density silicon probes combined with optogenetics", In Neuron, Apr. 2015, pp. 92-105.

Buzsaki, G., et al., "High-Frequency Network Oscillation in the Hippocampus", In Science, vol. 256, No. 5059, May 1992, pp. 1025-1027.

Buzsáki, G., et al., "Scaling Brain Size, Keeping Timing: Evolutionary Preservation of Brain Rhythms", In Neuron, vol. 80, No. 3, Oct. 30, 2013, pp. 751-764.

Buzsaki, G., et al., "The Origin of Extracellular Fields and Currents—EEG, ECoG, LFP and Spikes", In National Review of Neuroscience, vol. 13, No. 6, Jun. 2012, pp. 407-420.

Campana, A., et al., "Electrocardiogramith Conformable Organic Electrochemical Transistor Fabricated on Resorbable Bioscaffold", In Advanced Materials, vol. 26, No. 23, Jun. 2014, pp. 3874-3878.

Canolty, R.T, et al., "Oscillatory Phase Coupling Coordinates Anatomically Dispersed Funcitonal Cell Assemblies", In Proceedings of the National Academy of Sciences, vol. 107, No. 40, Sep. 2010, pp. 17356-17361.

Canolty, R.T., et al., "High Gamma Power Is Phase-Locked to Theta Oscillations in Human Neocortex", In Science, vol. 313, No. 5793, Sep. 15, 2006, pp. 1626-1628.

Cea, C., et al., "Enhancement-Mode Ion-Based Transistor as a Comprehensive Interface and Real-Time Processing Unit for In Vivo Electrophysiology", In Nature Materials, vol. 19, Mar. 16, 2020, pp. 1-11.

Challis, L. J., "Mechanisms for Interaction between RF Fields and Biological Tissue", In Bioelectromagnetics. Jun. 26, 2005, pp. S98-S106.

Chen, R., et al., "Neural Recording and Modulation Technologies", In Nature Review Materials, vol. 2, Feb. 2017, pp. 1-36.

Cheng, J.C., et al., "Lithographic Patterning of Immobilized Enzymes in Chitosan Thin Films for Multi-layer, Chemical/Biological Sensors", In Proceedings of the 7th IEEE Conference on Nanotechnology (IEEE NANO), Hong Kong, CN, Aug. 2-5, 2007, pp. 334-337.

Cho, J.H., et al., "High-Capacitance Ion Gel Gate Dielectrics with Faster Polarization Response Times for Organic Thin Film Transistors", In Advanced Materials, vol. 20, No. 4, Feb. 2008, pp. 686-690.

Choi, H.H., et al., "Critical Assessment of Charge Mobility Extraction in FETs", In Nature Materials, vol. 17, Jan. 2018, pp. 2-7.

Chung, H.U., et al., "Binodal, Wireless Epidermal Electronic Systems with In-Sensor Analytics for Neonatal Intensive Care", In Science, vol. 363, No. 6430, Mar. 2019, pp. 1-13.

Crispin, X., et al., "The Origin of the High Conductivity of Poly(3,4-ethylenedioxythiphene)-poly(styrenesulfonate)(PEDOT-PSS) Plastic Electrodes", In Chemistry of Materials, vol. 18, Sep. 2006, pp. 4354-4360.

Crone, B., et al., "Large-Scale Complementary Integrated Circuits Based on Organic Transistors", In Nature, vol. 403, Feb. 3, 2000, pp. 521-523.

Cui, X., and Martin, D.C., "Electrochemical Deposition and Characterization of Poly(3,4-ethylenedioxythiophene) on Neural Microelectrode Arrays", In Sensors Actuators B Chemical, vol. 89, Mar. 2003, pp. 92-102.

David, R., "A Photochemically 3D Printed High-Resolution Biodegradable Suture Retention Clip", Deep Blue Medical Advances, Inc., NIH Grant R43GM140802, last accessed Nov. 13, 2023, pp. 1-4, available at: https://reporter.nih.gov/search/QjIDxDQPNkiF33G76PERSQ/project-details/10157051.

Deisseroth, K., "Optogenetics: 10 Years of Microbial Opsins in Neuroscience", In Nature Neuroscience, vol. 18, Aug. 26, 2015, pp. 1213-1225.

Dennis, C., et al., "Suture Materials—Current and Emerging Trends", In Journal of Biomedical Materials Research Part A, vol. 104, No. 6, Jun. 2016, pp. 1544-1559.

Dimitrakopoulos, C.D. and Malenfant, P.R.L., "Organic Thin Film Transistors for Large Area Electronics", In Advanced Materials, vol. 14, No. 2, Jan. 17, 2002, pp. 99-117.

Duarah, R., et al., "Smart Self-Tightening Surgical Suture from a Tough Bio-Based Hyperbranched Polyurethane/Reduced Carbon Dot Nanocomposite", In Biomedical Materials, vol. 13, No. 4, Apr. 16, 2018, pp. 1-14.

Edis, Z., et al., ""Smart" Antimicrobial Nanocomplexes with Potential to Decrease Surgical Site Infections (SSI)", In Pharmaceutics, vol. 12, No. 4, Apr. 15, 2020, pp. 1-36.

(56) References Cited

OTHER PUBLICATIONS

Ellingson, R.J., "Electroencephalograms of Normal, Full-Term Newborns Immediately after Birth with Observations on Arousal and Visual Evoked Responses", In Electroencephalography and Clinical Neurophysiology, vol. 10, No. 1, Feb. 1958, pp. 31-50.
Ersman, P.A., et al., "Screen Printed Digital Circuits Based on Vertical Organic Electrochemical Transistors", In Flexible and Printed Electronics, vol. 2, No. 4, Nov. 3, 2017, pp. 1-13.
Fachetti, A., "Gels Excel", In Nature Materials, vol. 7, Nov. 2008, pp. 839-840.
Fang, H., et al., "Capacitively Coupled Arrays of Multiplexed Flexible Silicon Transistors for Long-Term Cardiac Electrophysiology", In Nature Biomedical Engineering, vol. 1, Mar. 2017, pp. 1-12.
Fang, H., et al., "Ultrathin, Transferred Layers of Thermally Grown Silicon Dioxide as Biofluid Barriers for Biointegrated Flexible Electronic Systems", In Proc. Natl. Acad. Sci. USA, vol. 113, No. 42, Oct. 17, 2016, pp. 11682-11687.
Fernandez-Ruiz, A., et al., "Long-Duration Hippocampal Sharp Wave Ripples Improve Memory", In Science, vol. 364, No. 6445, Jun. 14, 2019, pp. 1082-1086.
Feron, K., et al., "Organic Bioelectronics: materials and biocompatibility", In the International Journal of Molecular Sciences, vol. 19, No. 8, Aug. 2018, pp. 1-21.
Fuller, E.J., et al., "Parallel Programming of an Ionic Floating-Gate Memory Array for Scalable Neuromorphic Computing", In Science, vol. 364, No. 6440, Apr. 2019, pp. 570-574.
Gabriel, C., "Compilation of the Dielectric Properties of Body Tissues at RF and Microwave Frequencies", King's College London, UK, Physics Department, Jun. 1996, pp. 1-273.
Gagnon-Turcotte, G., et al., "A Wireless Optogenetic Headstage with Multichannel Electrophysiological Recording Capability", In Sensors, vol. 15, No. 9, Sep. 2015, pp. 22776-22797.
Gelinas, J.N., "Interictal Epileptiform Discharges Induce Hippocampal-Cortical Coupling in Temporal Lobe Epilepsy", In Nature Medicine, vol. 22, Apr. 2016, pp. 641-648.
Giovannitti, A., et al., "Controlling the Mode of Operation of Organic Transistors through Side-Chain Enginnering", In Proceedings of the National Academy of Sciences, vol. 113, No. 43, Oct. 10, 2016, pp. 12017-12022.
Gkoupidenis, P., et al., "Neuromorphic Device Architectures with Global Connectivity Through Electrolyte Gating", In Nature Communications, vol. 8, May 17, 2017, pp. 1-8.
Gogolla, N., et al., "Sensory Integration in Mouse Insular Cortex Reflects GABA Circuit Maturation", In Neuron, vol. 83, No. 4, Aug. 20, 2014, pp. 894-905.
Gonzalez Otarula, K.A., et al., "Automated Seizure Detection Accuracy for Ambulatory EEG Recordings", In Neurology, vol. 92, No. 14, Apr. 2019, pp. e1540-e1546.
Gou, Z., et al., "Resting Frontal Gamma Power at 16, 24 and 36 Months Predicts Individual Differences in Language and Cognition at 4 and 5 Years", In Behavioural Brain Research, vol. 220, No. 2, Feb. 3, 2011, pp. 263-270.
Grahame, D.C., "The Electrical Double Layer and the Theory of Electrocapillarity", In Chemical Reviews, vol. 41, No. 3, Dec. 1947, pp. 441-501.
Grunert, P., "From the Idea to its Realization: The evolution of minimally invasive techniques in neurosurgery", In Neuroendoscopy, vol. 2013, Dec. 2013, pp. 1-19.
Ha, M., et al., "Printed, Sub-3V Digital Circuits on Plastic from Aqueous Carbon Nanotube Inks", In ACS Nano, vol. 4, No. 8, Jun. 2010, pp. 4388-4395.
Hachisuka, K., et al., "Intra-Body Data Transmission for the Personal Area Network", In Microsystem Technologies, vol. 11, Jul. 2005, pp. 1020-1027.
Hamedi, M., et al., "Fiber-Embedded Electrolyte-Gated Field-Effect Transistors for e-Textiles", In Advanced Materials, vol. 21, No. 5, Feb. 2, 2009, pp. 573-577.

Harris, K. D., et al. "Accuracy of Tetrode Spike Separation as Determined by Simultaneous Intracellular and Extracellular Measurements", In Journal of Neurophysiology, Jul. 2000, pp. 401-414.
Harrison, R.R., et al., "Wireless Neural Recording with Single Low-Power Integrated Circuit", In IEEE Transactions on Neural Systems and Rehabilitation Engineering, vol. 17, No. 4, Jun. 2009, pp. 322-329.
Hiraizumi, Y., et al., "Application of Polyvinyl Alcohol Hydrogel Membrane as Anti-Adhesive Interposition After Spinal Surgery", In Spine, vol. 20, No. 21, Nov. 1995, pp. 2272-2277.
Hochberg, L.R., et al., "Neuronal Ensemble Control of Prosthetic Devices by a Human with Tetraplegia", In Nature, vol. 442, Jul. 13, 2006, pp. 164-171.
IEEE Standards Coordinating Committee, "IEEE Standard for Safety Levels with Respect to Human Exposure to Radio Frequency Electromagnetic Fields, 3 kHz to 300 GHz", In IEEE Std C95.1, 1999 Edition, vol. 6, Apr. 1999, pp. 1-83.
Il Chang, S., et al., "A Minimally-Invasive Neural Interface for Wireless Epidural Recording by Intra-Skin Communication", In IEEE Symposium VLSI Circuits, Digital Technical Papers, Jun. 2011, pp. 146-147.
Il Park, S., et al., "Soft, Stretchable, Fully Implantable Miniaturized Optoelectronic Systems for Wireless Optogenetics", In Nature Biotechnology, vol. 33, No. 12, Dec. 2015, pp. 1280-1286.
Imani, S., et al., "A Wearable Chemical-Electrophysiological Hybrid Biosensing System for Real-Time Health and Fitness Monitoring", In Nature Communications, vol. 7, May 2016, pp. 11650.
Inal, S., et al., "Benchmarking Organic Mixed Conductors for Transistors", In Nature Communications, vol. 8, Nov. 2017, pp. 1-7.
Inal, S.,et al., "A High Transconductance Accumulation Mode Electrochemical Transistor", In Advanced Materials, vol. 26, No. 44, Oct. 2014, pp. 7450-7455.
International Patent Application No. PCT/US2019/068363, filed Dec. 23, 2019, pp. 1-52.
International Preliminary Report on Patentability dated Jul. 1, 2021 in International Patent Application No. PCT/US2019/068363, pp. 1-8.
International Search Report and Written Opinion dated Apr. 7, 2020 in International Patent Application No. PCT/US2019/068363, pp. 1-160.
Itskov, V., "Theta-Mediated Dynamics of Spatial Information in Hippocampus", In the Journal of Neuroscience, vol. 28, No. 23, Jun. 2008, pp. 5959-5964.
Jastrzebska-Perfect, P., et al., "Mixed-Conducting Particulate Composites for Soft Electronics", In Science Advances, vol. 6, No. 17, Apr. 24, 2020, pp. 1-9.
Jastrzebska-Perfect, P., et al., "Translational Neuroelectronics", In Advanced Funcitonal Materials, vol. 30, No. 29, Jun. 2020, pp. 1-31.
Jeong, J.W., et al., "Soft Materials in Neuroengineering for Hard Problems in Neuroscience", In Neuron, vol. 86, No. 1, Apr. 8, 2015, pp. 175-186.
Jiang, H.L., et al., "Chitosan-Graft-Polyethylenimine as a Gene Carrier", In Journal of Controlled Release, vol. 117, No. 2, Feb. 12, 2007, pp. 273-280.
Jimison, L.H., et al., "Measurement of Barrier Tissue Integrity with an Organic Electrochemical Transistor", In Advanced Materials, vol. 24, No. 44, Nov. 20, 2012, pp. 5919-5923.
Jin, P., et al., "A Flexible, Stretchable System for Simultaneous Acoustic Energy Transfer and Communication", In Science Advances, Sep. 2021, pp. 1-13.
Jobst, B.C., et al., "Brain-Responsive Neurostimulation in Patients with Medically Intractable Seizures arising from Eloquent and Other Neocortical Areas", In Epilepsia, vol. 58, Apr. 2017, pp. 1005-1014.
Jun, J.J., et al., "Fully Integrated Silicon Probes for High-Density Recording of Neural Activity", In Nature, vol. 551, Nov. 9, 2017, pp. 232-236.
Kalidasan, V., et al., "Wirelessly Operated Bioelectronic Sutures for the Monitoring of Deep Surgical Wounds", In Nature Biomedical Engineering, vol. 5, No. 10, Oct. 2021, pp. 1-23.

(56) References Cited

OTHER PUBLICATIONS

Kaltenbrunner, M., et al., "An Ultra-Lightweight Design for Imperceptible Plastic Electronics", In Nature, vol. 499, Jul. 24, 2013, pp. 458-463.

Kappenman, E.S. and Luck, S.J., "The Effects of Electrode Impedance on Data Quality and Statistical Significance in ERP Recordings", In Psychophysiology, vol. 47, No. 5, Sep. 2010, pp. 888-904.

Khalifa, A., et al. "The Microbead: A Highly Miniaturized Wirelessly Powered Implantable Neural Stimulating System," In IEEE Transactions on Biomedical Circuits and Systems, Mar. 2018, pp. 521-531.

Khan, F., et al., "Versatile Biocompatible Polymer Hydrogels: Scaffolds for cell growth", In Angewandte Chemie International Edition, vol. 48, No. 5, Jan. 2009, pp. 978-982.

Khazipov, R., et al., "Early Motor Activity Drives Spindle Bursts in the Developing Somatosensory Cortex", Nature, vol. 432, Dec. 9, 2004, pp. 758-761.

Khodagholy, D., et al., "High Speed and High Density Organic Electrochemical Transistor Arrays", In Applied Physics Letters, vol. 99, No. 16, Oct. 17, 2011, pp. 1-4.

Khodagholy, D., et al., "High Transconductance Organic Electrochemical Transistors", In Nature Communications, vol. 4, Jul. 12, 2013, pp. 1-6.

Khodagholy, D., et al., "Highly Conformable Conducting Polymer Electrodes for In Vivo Recordings", In Advanced Materials, vol. 23, No. 26, Aug. 9, 2011, pp. 1-5.

Khodagholy, D., et al., "In Vivo Recordings of Brain Activity Using Organic Transistors", In Nature Communications, vol. 4, Mar. 12, 2013, pp. 1-7.

Khodagholy, D., et al., "NeuroGrid: recording action potentials from the surface of the brain", In Nature Neuroscience, vol. 18, No. 2, Feb. 2015, pp. 310-315.

Khodagholy, D., et al., "Organic Electronics for High-Resolution Electrocorticography of the Human Brain", In Science Advances, vol. 2, No. 11, Nov. 9, 2016, pp. 1-9.

Khodagholy, D., et al., "Learning-Enhanced Coupling Between Ripple Oscillations in Association Cortices and Hippocampus", In Science, vol. 372, No. 6361, Oct. 20, 2017, pp. 369-372.

Kim, C.Y., et al., "Soft Subdermal Implant Capable of Wireless Battery Charging and Programmable Controls for Applications in Optogenetics", In Nature Communications, vol. 12, Jan. 2021, pp. 1-13.

Kim, D.H., et al., "Stretchable and Foldable Silicon Integrated Circuits", In Science, vol. 320, No. 5875, Apr. 25, 2008, pp. 507-511.

Kim, K., et al., "A Carbon Nanotube Synapse with Dynamic Logic and Learning", In Advanced Materials, vol. 25, Mar. 2013, pp. 1693-1698.

Kim, S.H., et al., "Electrolyte-Gated Transistors for Organic and Printed Electronics", In Advanced Materials, vol. 25, No. 13, Apr. 2013, pp. 1822-1846.

Kim, Y., et al., "A Bioinspired Flexible Organit Artificial Afferent Nerve", In Science, vol. 360, No. 6392, Jun. 2018, pp. 998-1003.

King, R.W.P., et al., "The Electromagnetic Field of an Insulated Antenna in a Conducting Or Dielectric Medium", In IEEE Transactions on Microwave Theory Technology, vol. 31, No. 7, Jul. 1983, pp. 574-583.

Knopfmacher, O., et al., "Highly Stable Organic Polymer Field-Effect Transistor Sensor for Selective Detection in the Marine Environment", In Nature Communications, vol. 5, Jan. 6, 2014, pp. 1-9.

Krook-Magnuson, E., et al., "Neuroelectronics and Biooptics: Closed-Loop Technologies in Neurological Disorders", In JAMA Neurology, vol. 72, No. 7, Jul. 2015, pp. 823-829.

Lee, B., et al., "Single-Center Experience with the NeuroPace RNS System: A Review of Techniques and Potential Problems", In World Neurosurgery, vol. 84, No. 3, Sep. 2015, pp. 719-726.

Lee, J., et al., ", Neural Recording and Stimulation using Wireless Networks of Microimplants", In Nature Electronics, vol. 4, Aug. 2021, pp. 604-614.

Lee, J., et al., "Ion Gel Gated Polymer-Thin-Film Transistors", In Journal of the American Chemical Society, vol. 129, No. 15, Apr. 2007, pp. 4532-4533.

Lee, W., et al., "Transparent, Conformable Active Multielectrode Array using Organic Electochemical Transistors", In Proceedings of the National Academy of Sciences, vol. 114, No. 40, Sep. 2017, pp. 1-6.

Leonard, S., et al., "Smart Tissue Anastomosis Robot (STAR): A Vision-Guided Robotics System for Laparoscopic Suturing", In IEEE Transactions on Biomedical Engineering, vol. 61, No. 4, Apr. 2014, pp. 1305-1317.

Li, J., et al., "Body-Coupled Power Transmission and Energy Harvesting", In Nature Electronics, vol. 4, Jun. 2021, pp. 530-538.

Li, Q., et al., "Stable Thin-Film Ference Electrode on Plastic Substrate for All-Solid-State Ion-Sensitive Field-Effect Transistor Sensing System", In IEEE Electron Device Letters, vol. 38, No. 10, Oct. 2017, pp. 1469-1472.

Liang, W., et al., "A Multifunctional Green Antibacterial Rapid Hemostasis Composite Wound Dressing for Wound Healing", In Biomaterials Science, vol. 9, No. 21, Sep. 2021, pp. 7124-7133.

Lin, Z., et al., "A Work-Function Tunable Polyelectrolyte Complex (PEI:PSS) as a Cathode Interfacial layer for Inverted Organic Solar Cells", In Journal of Materials Chemistry, vol. 21, Jun. 2014, pp. 1-8.

Maingret, N., et al., "Hippocampo-Cortical Coupling Mediates Memory Consolidation During Sleep", In Nature Neuroscience, vol. 19, No. 7, May 16, 2016, pp. 1-19.

Malliaras, G.G., "Next-Generation Probes, Particles, and Proteins for Neural Interfacing", In Science Advances, vol. 3, No. 6, Jun. 9, 2017, pp. 1-20.

Meglinski, I. V., et al. "Quantitative Assessment of Skin Layers Absorption and Skin Reflectance Spectra Simulation in the Visible and Near-Infrared Spectral Regions", In Physiological Measurement, Oct. 2002, pp. 741-753.

Meng, X., et al., "Electrosynthesis of Pure Poly(3,4-ethylenedioxythiophene)(PEDOT) in Chitosan-Based liquid Crystal Phase", In Electronic Materials Letters, vol. 9, Sep. 2013, pp. 605-608.

Merletti, R., et al., "Analysis of Intramuscular Electromyogram Signals", In Philosophical Transactions of the Royal Society, vol. 367, No. 1887, Jan. 2009, pp. 1-14.

Mian, M.K., et al., "Deep Brain Stimulation for Obsessive-Compulsive disorder: Past, present, and future", In Journal of Neurosurgery, vol. 20, No. 2, Aug. 2010, pp. 1-9.

Minlebaev, M., et al., "Early Gamma Oscillations Synchronize Developing Thalamus and Cortex", In Science, vol. 334, No. 6053, Oct. 14, 2011, pp. 226-229.

Miranda, H., et al. "A High-Rate Long-Range Wireless Transmission System for Simultaneous Multichannel Neural Recording Applications", In IEEE Transactions Biomedical Circuits Systems, vol. 4, No. 3, Jun. 2010, pp. 181-191.

Morrell, M.J., "Responsive Cortical Stimulation for the Treatment of Medically Intracable Partial Epilepsy", In Neurology, vol. 77, No. 13, Sep. 2011, pp. 1295-1304.

Mostafalu, P., et al., "A Toolkit of Thread-Based Microfluidics, Sensors, and Electronics for 3D Tissue Embedding for Medical Diagnostics", Microsystems & Nanoengineering, vol. 2, No. 16039, Jul. 18, 2016, pp. 1-10.

Muller, R., et al., "A Minimally Invasive 64-Channel Wireless µECoG Implant", In IEEE Journal of Solid-State Circuits, vol. 50, No. 1, Nov. 2014, 344-359.

Nardes, A.M., et al., "A Morphological Model for the Solvent-Enhanced Conductivity of PEDOT:PSS Thin Films", In Advanced Functional Materials, vol. 18, No. 6, Mar. 26, 2008, pp. 865-871.

Nicolelis, M. A. L., et al., "Hebb's Dream: The Resurgence of Cell Assemblies", Neuron, vol. 19, Aug. 1997, pp. 219-221.

Nielsen, C.B., et al., "Molecular Design of Semiconducting Polymers for High-PErformance Organic Electrochemical Transistors", In the Journal of the American Chemical Society, vol. 138, No. 32, Jul. 2016, pp. 10252-10259.

Normann, R. A., et al., "A Neural Interface for a Cortical Vision Prosthesis", In Vision Research, vol. 39, No. 15, Jul. 1999, pp. 2577-2587.

(56) References Cited

OTHER PUBLICATIONS

Office Action dated Nov. 30, 2023 in U.S. Appl. No. 17/352,622, pp. 1-21.
Ono, S., et al., "A Comparative Study of Organic Single-Crystal Transistors Gated with Various Ionic-Liquid Electrolytes", In Applied Physics Letters, vol. 94, No. 6, Jan. 2009, pp. 1-5.
Panzer, M.J. and Frisbie, C.D., "Polymer Electrolyte-Gated Organic Field-Effect Transistors: low-voltage, high-current switches for organic electronics and testbeds for probing electrical transport at high charge carrier density", In the Journal of the American Chemical Society, vol. 129, No. 20, May 2007, pp. 6599-6607.
Panzer, M.J., et al., "Low-Voltage Operation of a Pentacene Field-Effect Transistor with a Polymer Electrolyte Gate Dielectric", In Appied. Physics Letters, vol. 86, No. 10, Jan. 2005, pp. 1-3.
Paulsen, B.D., et al., "Organic Mixed Ionic-Electronic Conductors", In Nature Materials, vol. 19, Jan. 2020, pp. 1-37.
Peyrache, A., et al., "Inhibition Recruitment in Prefrontal Cortex during Sleep Spindles and Gating of Hippocampal Inputs", In Proceedings of the National Academy of Sciences, vol. 108, No. 41, Sep. 2011, pp. 17207-17212.
Phan, P.T., et al., "Smart Surgical Sutures Using Soft Artificial Muscles", Scientific Reports, vol. 11, No. 1, Nov. 17, 2021, pp. 1-16.
Piech, D. K., et al., "A Wireless Millimetre-Scale Implantable Neural Stimulator with Ultrasonically Powered Bidirectional Communication", In Nature Biomedical Engineering, vol. 4, Feb. 2020, pp. 207-222.
Piech, D.K., et al., "Rodent Wearable Ultrasound System for Wireless Neural Recording", In Proceedings of the 39th Annual International Conference of the IEEE Engineering in Medicine and Biology Society (EMBC), Jeju, South Korea, Jul. 11-15, 2017, pp. 221-225.
Podzorov, V., "Organic Single Crystals: Addressing the fundamentals of organic electronics", In MRS Bulletin, vol. 38, No. 1, Jan. 2013, pp. 15-24.
Ramgopal, S., et al., "Seizure Detection, Seizure Prediction, and Closed-Loop Warning Systems in Epilepsy", In Epilepsy and Behavior, vol. 37, Aug. 2014, pp. 291-307.
Ramuz, M., et al., "Combined Optical and Electronic Sensing of Epithelial Cells using Planar Organic Transistors", In Advanced Materials, vol. 26, No. 41, Nov. 2014, pp. 7083-7090.
Ravi Kumar, M.N.V., "A Review of Chitin and Chitosan Applications", In Reactive and Functional Polymers, vol. 46, No. 1, Nov. 2000, pp. 1-27.
Reaz, M.B.I, et al., "Techniques of EMG Signal Analysis: Detection, processing, classification and applications", In Biological Procedures Online, vol. 8, Dec. 2006, pp. 11-35.
Rigante, S., et al., "Sensing with Advanced Computing Technology" Fin Field-Effect Transistors wtih High-k Gate Stack on Bulk Silicon, In ACS Nano, vol. 9, No. 5, Mar. 2015, pp. 4872-4881.
Rivnay, J., et al., "High-Performance Transistors for Bioelectronics through Tuning of Channel Thickness", In Science Advances, vol. 1, No. 4, May 2015, pp. 1-5.
Rivnay, J., et al., "Organic Electrochemical Transistors", In Nature Reviews Materials, vol. 3, Jan. 16, 2018, pp. 1-41.
Rivnay, J., et al., "Structural Control of Mixed Ionic and Electronic Transport in Conducting Polymers", In Nature Communications, vol. 7, Apr. 19, 2016, pp. 1-9.
Rivnay, J., et al., "The Rise of Organic Bioelectronics", Chemistry of Materials, vol. 26, No. 1, Jan. 14, 2014, pp. 679-685.
Rizk, M., et al., "A Single-Chip Signal Processing and Telemetry Engine for an Implantable 96-Channel Neural Data Acquisition System", In the Journal of Neural Engineering, vol. 4, No. 309, Sep. 2007, pp. 309-321.
Roberts, M.E., et al., "Water-Stable Organic Transistors and their Application in Chemical and Biological Sensors", In Proceedings of the National Academy of Science, vol. 105, No. 34, Aug. 26, 2008, pp. 12134-12139.
Rogers, J.A., et al., "Materials and Mechanics for Stretchable Electronics", In Science, vol. 327, No. 5973, Mar. 26, 2010, pp. 1603-1607.
Rohenkohl, G., et al., "Gamma Synchronization between V1 and V4 Improves Behavioral Performance", In Neuron, vol. 100, No. 4, Oct. 11, 2018, pp. 1-15.
Rosell, J., et al., "Skin Impedance from 1 Hz to 1 MHz", In IEEE Transactions Biomedical Engineering, vol. 35, No. 8, Aug. 1988, pp. 649-651.
Said, E., et al., "Effects of the Ionic Currents in Electrolyte-gated Organic Field-Effect Transistors", In Advanced Functional Materials, vol. 18, No. 21, Nov. 10, 2008, pp. 3529-3536.
Sani, N., et al., "All-Printed Diode Operating at 1.6GHz", In Applied Physical Sciences, vol. 111, No. 33, Jul. 2014, pp. 11943-11948.
Schmode, P., et al., "High-Performance Organic Electrochemical Trasnistors Based on Conjugated Polyelectrolyte Copolymers", In Chemistry of Materials, vol. 31, No. 14, Jun. 2019, pp. 5286-5295.
Seelke, A.M.H., and Blumberg, M.S., "Developmental Appearance and Disappearance of Cortical Events and Oscillations in Infant Rats", In Brain Research, vol. 1324, Feb. 6, 2010, pp. 34-42.
Seo, D., et al., "Wireless Recording in the Peripheral Nervous System with Ultrasonic Neural Dust", In Neuron, vol. 91, Aug. 2016, pp. 528-539.
Sessolo, M., et al., "Easy-to-Fabricate Conducting Polymer Microelectrode Arrays", In.Advanced Materials, vol. 25, No. 15, Feb. 2013, pp. 2135-2139.
Seymour, J.P., and Kipke, D.R., "Neural Probe Design for Reduced Tissue Encapsulation in CNS", In Biomaterials, vol. 28, No. 25, Apr. 9, 2007, pp. 3594-3607.
Sheliakina, M., et al., "An All-Solid-State Biocompatible Ion-to-Electron Transducer for Bioelectronics", In Materials Horizons, vol. 5, Jan. 17, 2018, pp. 256-263.
Shimotani, H., et al., "Electrolyte-Gated Charge Accumulation in Organic Single Crystals", In Applied Physics Letters, vol. 89, No. 20, Sep. 2006, pp. 1-4.
Sirota, A., et al., "Entrainment of Neocortical Neurons and Gamma Oscillations by the Hippocampal Theta Rhythm", In Neuron, vol. 60, No. 4, Nov. 26, 2008, pp. 1-15.
Sodagar, A.M., et al., "An Implantable Microsystem for Wireless Multi-Channel Cortical Recording", In Proceedings of TRANSDUCERS 2007 International Solid-State Sensors, Actuators and Microsystems Conference, Lyon, France, Jun. 10-14, 2007, pp. 69-72.
Someya, T., et al., "A Large-Area, Flexible Pressure Sensor Matrix with Organic Field-Effect Transistors for Artificial Skin Applications", In Proceedings of the National Academy of Science USA., vol. 101, No. 27, Jul. 6, 2004, pp. 9966-9970.
Someya, T., et. al., "The Rise of Plastic Bioelectronics", In Nature, vol. 540, Dec. 2016, pp. 379-385.
Song, C., et al., "An Injectable Conductive Three-Dimensional Elastic Network by Tangled Surgical-Suture Spring for Heart Repair", In ACS Nano, vol. 13, No. 12, Dec. 2019, pp. 14122-14137.
Song, E., et al., "Flexible Electronic/Optoelectronic Microsystems with Scalable Designs for Chronic Biointegration", In Proceedings of the National Academy of Sciences, vol. 116, No. 31, Jul. 15, 2019, pp. 15398-15406.
Spyropoulos, G., et al., "Internal Ion-Gated Organic Electrochemical Transistor: A building block for integrated bioelectronics", Science Advances, vol. 5, No. 2, Feb. 27, 2019, pp. 1-9.
Spyropoulos, G., et al., "Organic and Perovskite Solar Modules Innovated By Adhesive Top Electrode and Depth-Resolved Laser Patterning", In Energy & Environmental Sciences, vol. 9, No. 7, Jul. 1, 2016, pp. 2302-2313.
Stavrinidou, E., et al., "Electronic Plants", In Science Advances, vol. 1, No. 10, Nov. 20, 2015, pp. 1-9.
Strakosas, X., et al., "The Organic Electrochemical Transistor for Biological Applications", In the Journal of Applied Polymer Science, vol. 132, No. 15, Apr. 2015, pp. 1-14.
Stravrinidou, E., et al., "Direct Measurement of Ion Mobility in a Conducting Polymer", In Advanced Materials, vol. 25, No. 32, Jun. 20, 2013, pp. 4488-4493.

(56) References Cited

OTHER PUBLICATIONS

Szuts, T.A., et al., "A Wireless Mutli-Channel Neural Amplifier for Freely Moving Animals", In Nature Neuroscience, vol. 14, Jan. 2011, pp. 263-269.
Takashima, W., et al., "Electroplasticity Memory Devices Using Conducting Polymers and Solid Polymer Electrolytes", In Polymer International, vol. 27, No. 3, Jan. 1, 1992, pp. 249-253.
Tang, N., et al., "Highly Efficient Self-Healing Multifunctional Dressing with Antibacterial Activity for Sutureless Wound Closure and Infected Wound Monitoring", In Advanced Materials, vol. 34, No. 3, Nov. 5, 2021, pp. 1-12.
Topalovic, U., et al., "Wireless Programmable Recording and Stimulation of Deep Brain Activity in Freely Moving Humans", In Neuron, vol. 108, No. 2, Oct. 2020, pp. 322-334.e9.
Tria, S.A., et al., "Dynamic Monitoring of Salmonella Typhimurium Infection of Polarized Epithelia using Organic Transistors", In Advanced Healthcare Materials, vol. 3, No. 7, Jul. 2014, pp. 1053-1060.
Tsumura, A., et al., "Macromolecular Electronic Device: Field-Effect Transistor with a Polythiophene Thin Film", In Applied Physics Letters, vol. 49, Nov. 1986, pp. 1210-1212.
Tybrandt, K., et al., "Chemical Potential-Electric Double Layer Coupling in Conjugated Polymer-Polyelectrolyte Blends", In Science Advances, vol. 3, No. 12, Dec. 2017, pp. 1-7.
Tybrandt, K., et al., "High-Density Stretchable Electrode Grids for Chronic Neural Recording", Advanced Materials, vol. 30., No. 15, Feb. 28, 2018, pp. 1-7.
Tybrandt, K., et al., "Logic Gates Based on Ion Transistors", In Nature Communications, vol. 3, May 29, 2012, pp. 871-876.
U.S. Appl. No. 17/352,622, filed Jun. 21, 2021, pp. 1-30.
U.S. Appl. No. 18/106,467, filed Feb. 6, 2023, pp. 1-23.
U.S. Appl. No. 18/118,044, filed Mar. 6, 2023, pp. 1-17.
U.S. Appl. No. 62/784,315, filed Dec. 21, 2018, pp. 1-44.
U.S. Appl. No. 62/900,633, filed Sep. 15, 2019, pp. 1-28.
U.S. Appl. No. 62/952,692, filed Dec. 23, 2019, pp. 1-93.
U.S. Appl. No. 63/307,152, filed Feb. 6, 2022, pp. 1-28.
U.S. Appl. No. 63/316,986, filed Mar. 5, 2022, pp. 1-47.
van de Burgt, Y., et al., "A Non-Volatile Organic Electrochemical Device As A Low-Voltage Artificial Synapse For Neuromorphic Computing", In Nature Materials, vol. 16, Feb. 20, 2018, pp. 414-418.
van der Pol, T., "Controlling the Doping Level in a Conducting Polymer for Application in Enhancement Mode Organic Electrochemical Transistors", Technical Report, Eindhoven University of Technology, Feb. 2018, pp. 1-72.
Vaz, A., et al., "Coupled Ripple Oscillations between the MTL and Neocortex retreive Human Memory", In Science, vol. 363, No. 6430, Mar. 2019, pp. 975-978.
Velliste, M., et al., "Cortical Control of a Prosthetic Arm for Self-Feeding", In Nature, vol. 453, May 28, 2008, pp. 1098-1101.
Venkatraman, V., et al., "Subthreshold Operation of Organic Electrochemical Transistors for Biosignal Amplification", In Advanced Science, vol. 5, Jul. 4, 2018, pp. 1-7.
Vetter, R.J., et al., "Chronic Neural Recording Using Silicon-Substrate Microelectrode Arrays Implanted in Cerebral Cortex", In IEEE Transactions on Biomedical Engineering, vol. 51, No. 6, Jul. 2011, pp. 896-904.
Viventi, J., et al., "Flexible, Foldable, Actively Multiplexed, High-Density Electrode Array for Mapping Brain Activity in Vivo", In Nature Neuroscience, vol. 14, Nov. 2011, pp. 1599-1605.
Voelker, M. and Fromherz, P., "Signal Transmission from Individual Mammalian Nerve Cell to Field-Effect Transistor", In Small, vol. 1, No. 2, Feb. 2005, pp. 206-210.
Voloh, B., et al., "Theta-Gamma Coordination Between Anterior Cingulate and Prefrontal Cortex Indexes Correct Attention Shifts", In Proceedings of the National Academy of Sciences, vol. 112, No. 27, Jun. 22, 2015, pp. 8457-8462.
Voroslakos, M., et al., "Direct Effects of Transcranial Electric Stimulation on Brain Circuits in Rats and Humans", In Nature Communications, vol. 9, Feb. 2, 2018, pp. 1-17.
Wang, S., et al., "Chitosan/Gelatin Porous Scaffolds Assembled with Conductive Poly(3,4-ethylenedioxythiophene) Nanoparticles for Neural Tissue Engineering", In Journal of Materials Chemistry, vol. 24, May 2017, pp. 4774-4788.
Wellman, S. M., et al., "A Materials Roadmap to Functional Neural Interface Design", In Advanced Functional Materials, Jul. 19, 2017, pp. 1-38.
White, H.S., et al., "Chemical Derivatization of an Array of Three Gold Microelectrodes with Polypyrrole: Fabrication of a Molecule-based Transistor", In Journal of the American Chemical Society, vol. 106, No. 18, Sep. 1, 1984, pp. 5375-5377.
Wilson, M.A., and McNaughton, B.L., "Dynamics of the Hippocampal Ensemble Code for Space", In Science, vol. 261, No. 5124, Aug. 20, 1993, pp. 1055-1058.
Wimmer, R.D., et al., "Sustaining Sleep Spindles through Enhanced SK2-Channel Activity Consolidates Sleep and Elevates Arousal Threshold", In the Journal of Neuroscience, vol. 32, No. 40, Oct. 2012, 13917-13928.
Won, S.M., et al., "Wireless and Battery-Free Technologies for Neuroengineering", In Nature Biomedical Engineering, Mar. 2021, pp. 405-423.
Xuan, Y., et al., "An All-Polymer-Air PEDOT Battery", In Organic Electronics, vol. 13, No. 4, Apr. 2012, pp. 632-637.
Yang, J. W., et al., "Three Patterns of Oscillatory Activity Differentially Synchronize Developing Neocortical Networks in Vivo", In Journal of Neuroscience, vol. 29, No. 28, Jul. 15, 2009, pp. 9011-9025.
Yang, S.Y., et al., "Integration of a Surface-Directed Microfluidic System with an Organic Electrochemical Transistor Array for Multi-Analyte Biosensors", In Lab on a Chip, vol. 9, No. 5, Mar. 7, 2009, pp. 704-708.
Yin, M. and Ghovanloo, M., "A Low-Noise Clockless Simultaneous 32-Channel Wireless Neural Recording System with Adjustable Resolution", In Analog Integrated Circuits and Signal Processing, vol. 66, Mar. 2011, pp. 417-431.
Yin, M., et al., "Wireless Neurosensor for Full-Spectrum Electrophysiology Recordings during Free Behavior", In Neuron, Dec. 2014, pp. 1170-1182.
Zare Bidoky, F., et al., "Sub-3 V ZnO Electrolyte-Gated Transistors and Circuits with Screen-Printed and Photo-Crosslinked Ion Gel Gate Dielectrics: new Routes to Improved Performance", In Advanced Functional Materials, vol. 30, No. 20, May 2019, pp. 1-26.
Zeglio, E., et al., "Conjugated Polyelectrolyte Blends for Electrochromic and Electrochmical Transistor Devices", In Chemistry of Materials, vol. 27, No. 18, Aug. 2015, pp. 6385-6393.
Zhang, S., et al., "Solvent-Induced Changes in PEDOT:PSS Films for Organic Electrochemical Transistors", In APL Materials, vol. 3, Dec. 30, 2014, pp. 1-8.
Zhao, Z., et al., "Responsive Manipulation of Neural Circuit Pathology by Fully Implantable, Front-End Multiplexed Embedded Neuroelectronics", In Proceedings of the National Academy of Sciences, vol. 118, No. 20, May 2021, pp. 1-9.
Zhou, A., et al., "A Wireless and Artefact-Free 128-Channel Neuromodulation Device for Closed-Loop Stimulation and Recording in Non-Human Primates", In Nature Biomedical Engineering, Dec. 2018, pp. 14-28.
Zhou, Y., et al., "A Universal Method to Produce Low-Work Function Electrodes for Organic Electronics", In Science, vol. 336, No. 6079, Apr. 2012, pp. 327-332.
Zimmerman, T.G., "Personal Area Networks: Near-field intrabody communication", In IBM Systems Journal, vol. 35, No. 3.4, Mar. 1996, pp. 1-81.
Zozoulenko, I., et al., "Polarons, Bipolarons, and Absorption Spectroscopy of PEDOT", In ACS Applied Polymer Materials, Jan. 2019, pp. 83-94.

* cited by examiner

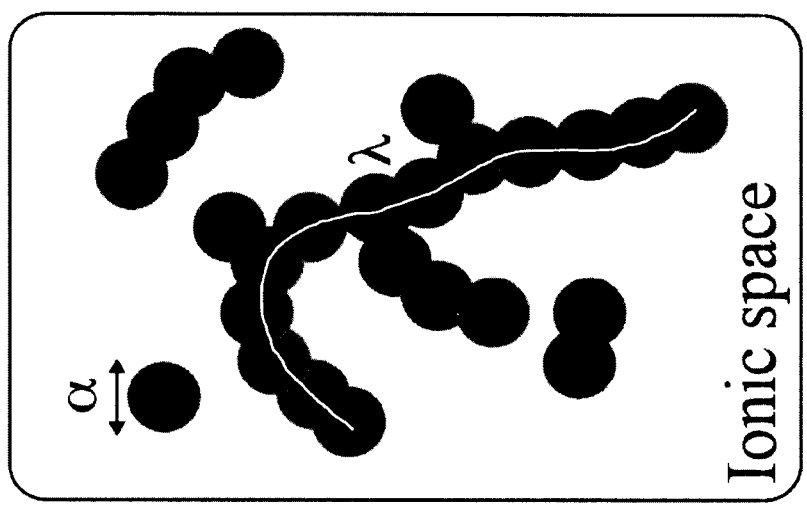
FIG. 1A1

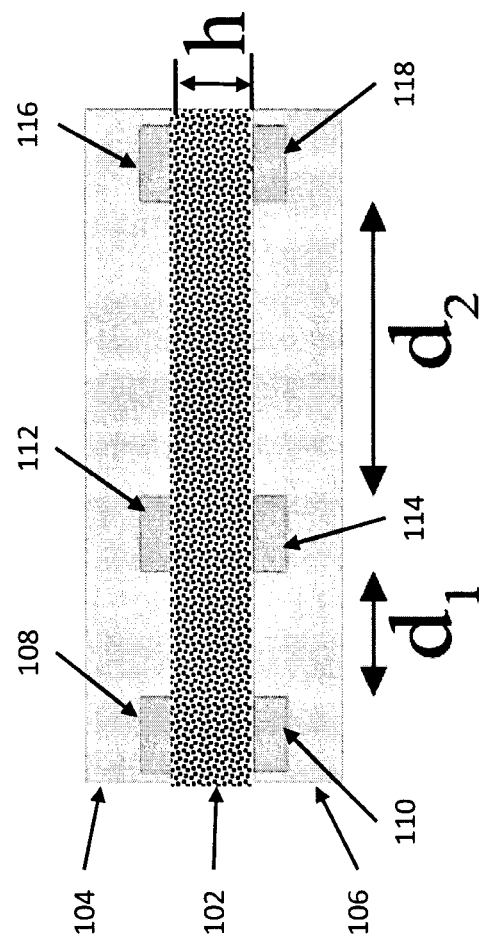
FIG. 1A2

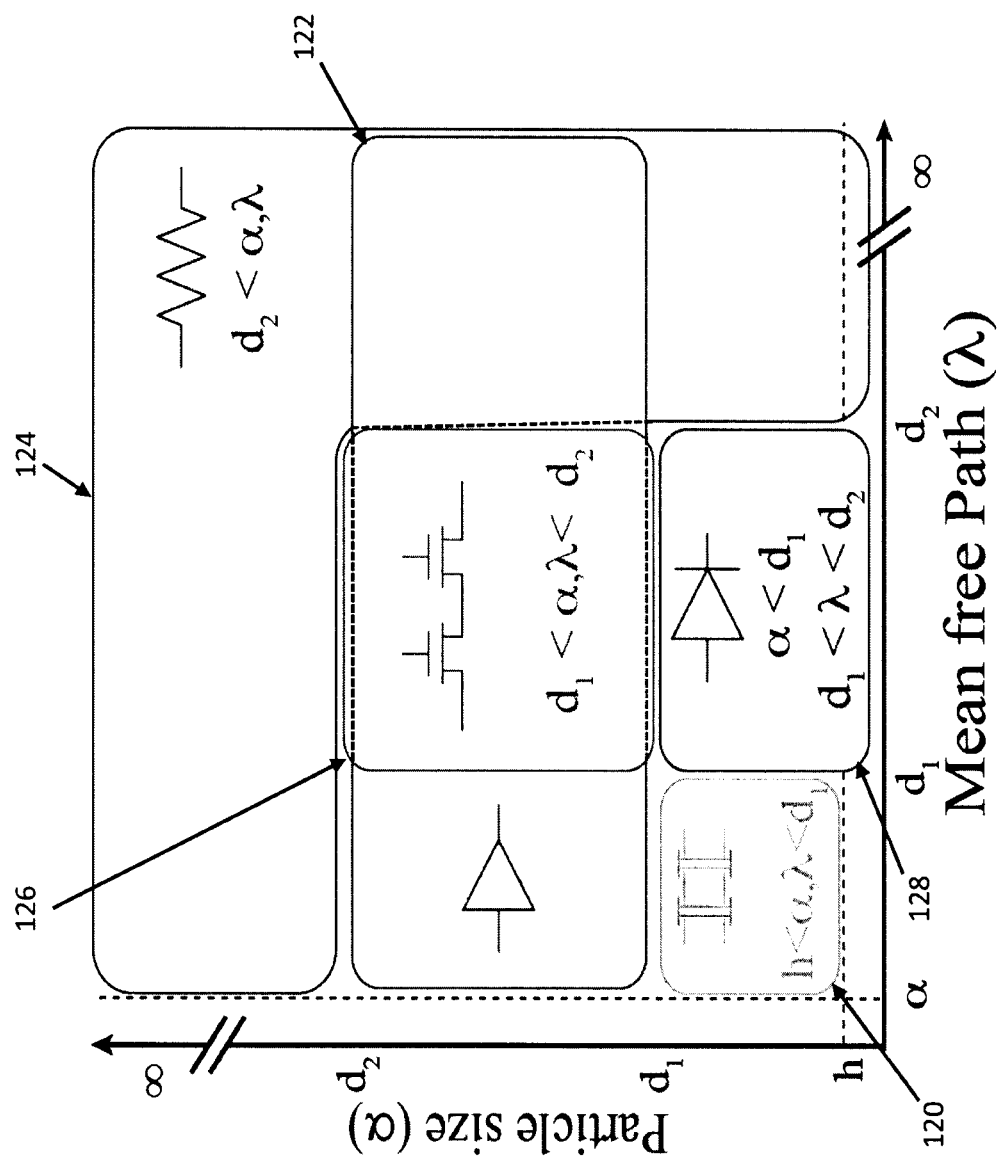
FIG. 1A3

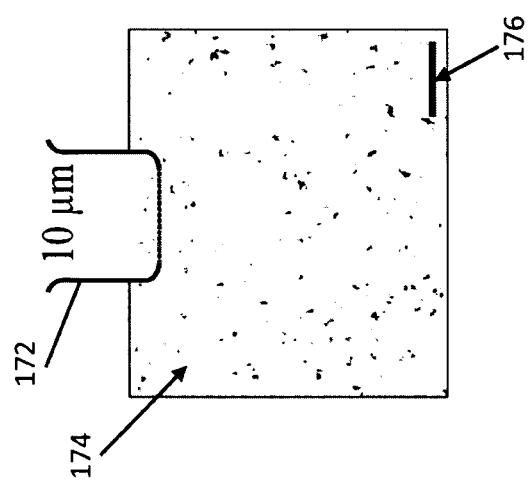
FIG. 1C1

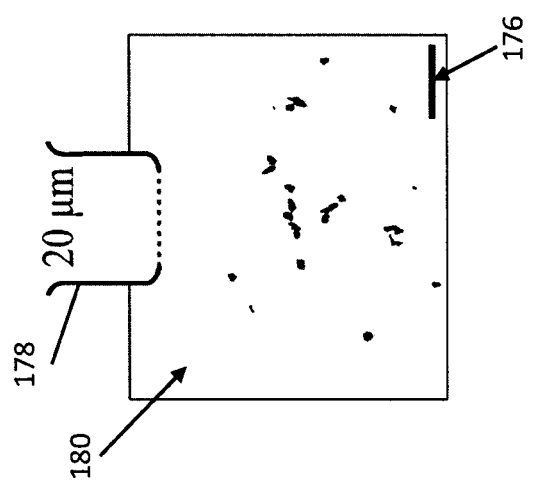
FIG. 1C2

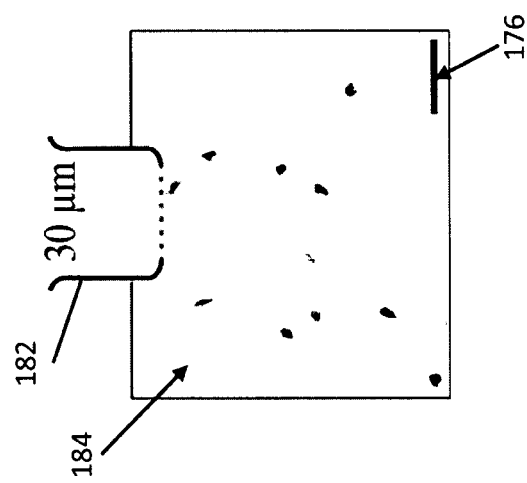
FIG. 1C3

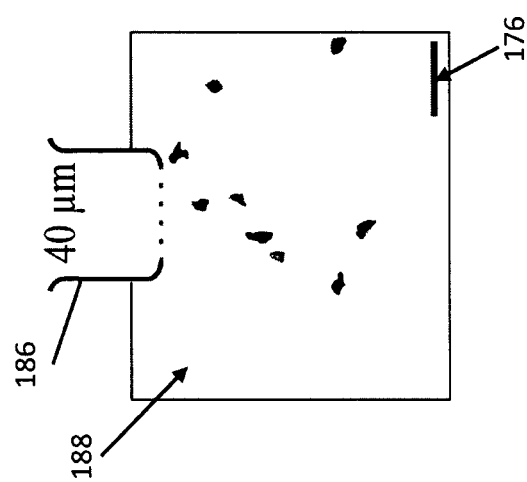
FIG. 1C4

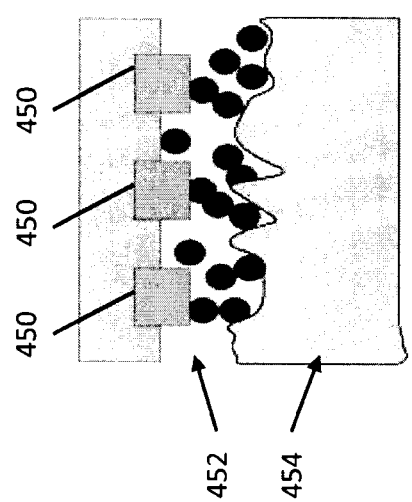

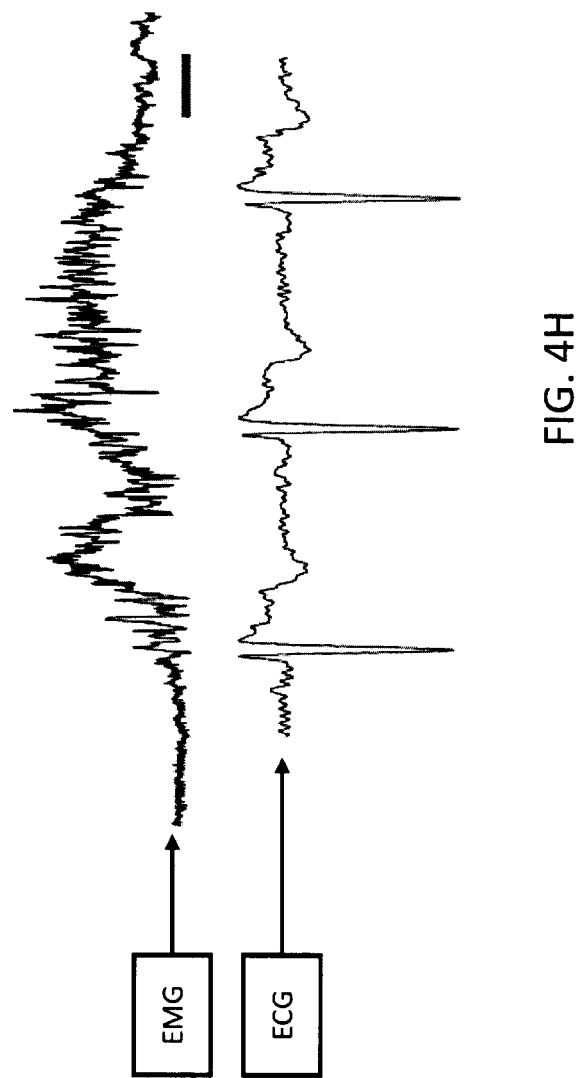

COMPOSITES AND DEVICES FOR INTERFACING ELECTRONICS TO BIOLOGICAL TISSUE

CROSS REFERENCE TO RELATED APPLICATION

This application claims the benefit of U.S. Provisional Patent Application No. 62/900,633, filed Sep. 15, 2019, which is hereby incorporated by reference herein in its entirety.

BACKGROUND

For a variety of reasons, it is desirable to interface electronics to biological tissue. For example, it is desirable to be able to interface electronics to people and animals for the purposes of diagnostics and medical treatment.

Current devices for interfacing electronics to biological tissue are inadequate.

For example, high spatiotemporal resolution conformable probes are increasingly being used to acquire signals from biological tissues, and similar resolution rigid electronics exist to process these signals. However, current techniques to enable transmission of signals between the soft probe and hard electronics (e.g., thermal bonding or sonic metal-metal bonding, metal/epoxy composite pastes) are not biocompatible or scalable, and introduce additional rigidity and bulk.

As another example, conventional electrodes designed to acquire electrophysiologic signals from the skin typically rely on ionic gels to form an appropriate impedance interface with the skin. These gels are not amenable to patterning and their spread across the skin surface is difficult to control, limiting the spatial resolution of activity that can be acquired non-invasively.

Accordingly, new mechanisms for interfacing electronics to biological tissue are desirable.

SUMMARY

In accordance with some embodiments, mechanisms (which can include composites, methods, and devices) for interfacing electronics to biological tissue are provided. In some embodiments, composites, are provided, the composites comprising: mixed conducting particles; and an ion conducting scaffolding matrix. In some of these embodiments, the mixed conducting particles are made from poly (3,4-ethylenedioxythiophene)-poly(styrenesulfonate). In some of these embodiments, the ion conducting scaffolding matrix includes a chitosan (CS)-based polymer.

In some embodiments, devices are provided, the devices comprising: a composite comprising mixed conducting particles and an ion conducting scaffolding matrix; and three electrodes, wherein: each of the three electrodes is in contact with the composite; a first pair of the three electrodes are on opposite sides of the composite and are a distance h apart; a second pair of the three electrodes are on a same side of the composite and are a distance d1 apart; a particle size of the mixed conducting particles is between h and d1; a mean-free-path of the mixed conducting particles is less than d1; and the composite behaves like an anisotropic conductor.

In some embodiments, devices are provided, the devices comprising: a composite comprising mixed conducting particles and an ion conducting scaffolding matrix; and three electrodes, wherein: each of the three electrodes is in contact with the composite; the three electrodes are on a same side of the composite; a first pair of the three electrodes are a distance d1 apart; a second pair of the three electrodes are a distance d2 apart, where d2 is greater than d1; a particle size of the mixed conducting particles is between d1 and d2; and the composite behaves like an ionic transistor.

In some embodiments, devices are provided, the devices comprising: a composite comprising mixed conducting particles and an ion conducting scaffolding matrix; and three electrodes, wherein: each of the three electrodes is in contact with the composite; the three electrodes are on a same side of the composite; a first pair of the three electrodes are a distance d1 apart; a second pair of the three electrodes are a distance d2 apart, where d2 is greater than d1; and the composite behaves like a resistor, and wherein at least one of: a particle size of the mixed conducting particles is greater than d2; and a mean-free-path of the mixed conducting particles is less than d1.

In some embodiments, devices are provided, the devices comprising: a composite comprising mixed conducting particles and an ion conducting scaffolding matrix; and three electrodes, wherein: each of the three electrodes is in contact with the composite; the three electrodes are on a same side of the composite; a first pair of the three electrodes are a distance d1 apart; a second pair of the three electrodes are a distance d2 apart, where d2 is greater than d1; a particle size of the mixed conducting particles is between d1 and d2; a mean-free-path of the mixed conducting particles is between d1 and d2; and the composite behaves like an independently gated ionic transistor.

In some embodiments, devices are provided, the devices comprising: a composite comprising mixed conducting particles and an ion conducting scaffolding matrix; and three electrodes, wherein: each of the three electrodes is in contact with the composite; the three electrodes are on a same side of the composite; a first pair of the three electrodes are a distance d1 apart; a second pair of the three electrodes are a distance d2 apart, where d2 is greater than d1; a particle size of the mixed conducting particles is less than d1; a mean-free-path of the mixed conducting particles is between d1 and d2; and the composite behaves like a diode.

BRIEF DESCRIPTION OF THE DRAWINGS

FIG. 1A1 is an example illustration of a diameter ($\alpha$) and a mean-free-path ($\lambda$) of mixed conducting particles in an ionic space in accordance with some embodiments.

FIG. 1A2 is an example of a schematic of a particulate mixed-conducting composite placed in between a substrate top layer having electrodes and a substrate bottom layer having electrodes in accordance with some embodiments.

FIG. 1A3 is an example graph showing that particulate mixed-conducting composites can provide different functional modes of operation depending on the combination of the particle size (diameter)($\alpha$) and the mean free path ($\lambda$) of mixed-conducting particles in the composites in accordance with some embodiments.

FIGS. 1C1-1C4 are example illustrations of sieving mixed-conducting particles in accordance with some embodiments.

FIG. 4G is an example of a schematic showing gold-based electrodes coated with a layer of a particulate mixed conducting composite applied to a person's skin in accordance with some embodiments.

FIG. 4H is an example of sample traces of a particulate mixed conducting composite-acquired EMG (top) and ECG (bottom) measured in accordance with some embodiments.

DETAILED DESCRIPTION

Figure 1B:
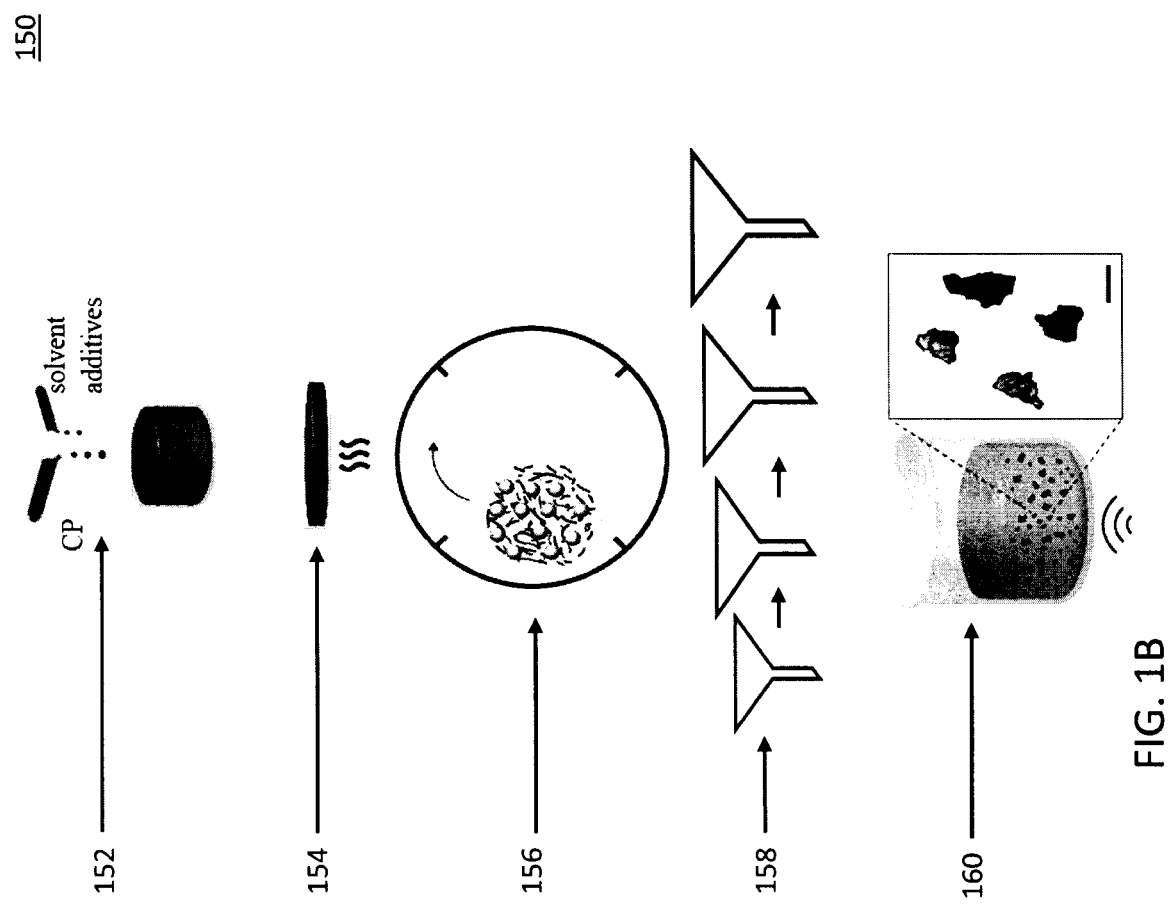
FIG. 1B is an example illustration of a process for forming mixed-conducting particles in accordance with some embodiments.

In accordance with some embodiments, mechanisms, which can include composites, methods, and devices, for interfacing electronics to biological tissue are provided. More particularly, in some embodiments, particulate mixed-conducting composites for interfacing electronics to biological tissue are provided.

In some embodiments, these particulate mixed-conducting composites include mixed-conducting particles in an ion conducting scaffolding polymer matrix that enable electronics to be interfaced to biological tissue. In some embodiments, this is accomplished by controlling the sparsity and the size of the mixed-conducting particles within a scaffolding polymer matrix that has controllable ionic conductivity.

In some embodiments, the particulate mixed-conducting composites allows a single material to function as multiple different principle electronic components. In some embodiments, the particulate mixed-conducting composites also eliminate the need for several bonded layers of patterned conducting, semiconducting, and insulating materials in order to provide multiple different principle electronic components.

In some embodiments, key properties of the particulate mixed-conducting composites are the mean diameter ($\alpha$) of the mixed-conducting particles and the density ($\rho$) of the mixed-conducting particles in the ion conducting scaffolding polymer matrix. The mean diameter $\alpha$ and density $\rho$ interact to determine the longest electrically conducting length that the particles can form (mean-free-path, $\lambda$). In some embodiments, the mean-free-path $\lambda$ is proportional to mean diameter a multiplied by the density $\rho$. An example illustration of diameter ($\alpha$) and mean-free-path ($\lambda$) in accordance with some embodiments is shown in FIG. 1A1

In some embodiments, as shown in FIG. 1A2, the particulate mixed-conducting composites 102 can be placed in between a substrate top layer 104 having electrodes 108, 112, and 116 and a substrate bottom layer 106 having electrodes 110, 114, and 118. As also shown, in some embodiments, the distance between the electrodes in top layer 104 and the electrodes in bottom layer 106 can be defined as distance h, the shortest distance between adjacent electrodes (e.g., the distances between electrodes 108 and 112 and between electrodes 110 and 114) can be defined as distance $d_1$, and the longest distance between electrodes (e.g., the distances between electrodes 112 and 116 and between electrodes 114 and 118) can be defined as distance $d_2$.

In some embodiments, as shown in FIG. 1A3 by regions 120, 122, 124, 126, and 128, the particulate mixed-conducting composites can provide different functional modes of operation depending on the combination of the particle size (diameter)($\alpha$) and the mean free path ($\lambda$) of the mixed-conducting particles relative to distances $d_1$, $d_2$, and h.

More particularly for example, as shown by region 120, a particulate mixed-conducting composite can behave as an anisotropic conductor in some embodiments. This can occur when the particle size $\alpha$ and the density $\rho$ of the particles result in a mean free path $\lambda$ that is shorter than the distance $d_1$ and the particle size $\alpha$ is between distance h and distance $d_1$. This is the case in some embodiments because: when the mean free path $\lambda$ is shorter than the distance $d_1$, the possibility of lateral electric conduction is eliminated because no continuous electrical path can be formed by the particles; and when the particle size $\alpha$ is also approximately equal to the distance h, selective vertical conduction will occur.

As another example, as shown by region 122, a particulate mixed-conducting composite can behave as an ionic transistor in some embodiments. This can occur when the particle size $\alpha$ and the density $\rho$ of the particles result in a mean free path $\lambda$ that is longer than distance $d_1$ that defines the transistor's channel length. This is the case in some embodiments because, when the particle size is large enough to bridge distance $d_1$, the particles form a transistor channel that can be doped and/or dedoped by the ionic conducting scaffolding polymer matrix when a voltage is applied.

As still another example, as shown by region 124, a particulate mixed-conducting composite can behave as a resistor in some embodiments. This can occur when the particle size a is greater than the distance $d_2$ and/or the particle size $\alpha$ and the density $\rho$ of the particles result in a mean free path $\lambda$ that is longer than the distance $d_2$. This is the case in some embodiments because when the particle size is orders of magnitude longer than $d_1$ and/or the mean free path $\lambda$ is orders of magnitude longer than the distance $d_1$, resistive electronic properties will dominate the interaction and the composite will approach the properties of a conducting polymer.

As yet another example, as shown by region 126, a particulate mixed-conducting composite can behave as an independently gated ionic transistor in some embodiments. This can occur when the particle size $\alpha$ is between the distance $d_1$ and the distance $d_2$ and the mean free path $\lambda$ is between the distance $d_1$ and the distance $d_2$. In this case, the gate to channel distance is defined by distance $d_2$ while channel length is distance $d_1$. This is the case in some embodiments because: increasing the particle size $\alpha$ or the density $\rho$ to create a mean free path $\lambda$ that is longer than the distance $d_1$ but shorter than the distance $d_2$ allows for independent gating of the ionic transistor; and particles bridging the distance $d_1$ form a transistor channel, which has ionic interaction with the gate electrode located at the distance $d_2$ through the scaffolding polymer matrix. In this manner, addressable transistors can be formed without channel patterning in some embodiments.

As still another example, as shown by region 128, a particulate mixed-conducting composite can behave as a diode in some embodiments. This can occur when the particle size $\alpha$ is less than the distance $d_1$ and the particle size $\alpha$ and the density $\rho$ of the particles result in a mean free path $\lambda$ that is between the distance $d_1$ and the distance $d_2$. This can be the case in some embodiments because when the particle size $\alpha$ is substantially less than the distance $d_1$, but the mean free path $\lambda$ is approximately equal to the distance $d_1$, a diode is created. Particle chains that are in contact with the electrodes and span the distance $d_1$ (bridging particle chains) permit electronic conduction to occur between the terminals. However, particle chains that are omnidirectionally located within the scaffolding polymer matrix will induce ion conduction and dope and/or dedope the bridging particles, resulting in a nonlinear relationship between applied voltage and conduction.

An example of a process of preparing particulate mixed conducting composites is now provided.

In some embodiments, mixed conducting particles can be formed by example process 150 as shown in FIG. 1B.

As illustrated, beginning at 152, a conducting dispersion of a conducting polymer, including additives and cross-linkers to maximize conductivity and stability, can be formed. Any suitable conducting polymer, additives, and crosslinkers can be used in some embodiments. For example, in some embodiments, a highly conducting dispersion of the conducting polymer poly(3,4-ethylenedioxythiophene)-poly(styrenesulfonate) (PEDOT:PSS) can be used. More particularly, for example, in some embodiments, a high-conductivity PEDOT:PSS can be prepared by mixing 80% PEDOT:PSS, 20% ethylene glycol, and 0.6% DBSA (all v/v). PEDOT:PSS (CleviosTM PH 1000) is available from Heraeus Deutschland GmbH & Co. KG of Leverkusen, Germany. Ethylene glycol, 4-dodecyl benzene sulfonic acid (DBSA), and poly(styrene sulfonate) are available from MilliporeSigma of St. Louis, MO.

Next, at 154, the dispersion can be evaporated over a large surface area to create dried, highly conductive sheets. This dispersion can be evaporated in any suitable manner, and these sheets can have any suitable thickness, such as a thickness of less than 50 μm, in some embodiments. More particularly, for example, in some embodiments, high-conductivity PEDOT:PSS mixed with 1% v/v of 3-glycidoxypropyltrimethoxysilane (GOPS) can be cast into a glass petri dish and dehydrated for eight to sixteen hours at 120° C. (or any other suitable temperature) in a well-ventilated environment. 3-glycidyloxypropyltrimethoxysilane (GOPS) is available from MilliporeSigma of St. Louis, MO.

Then, at 156, the resulting film can be cut into small fragments and crushed in a bead mill. This can be performed in any suitable manner in some embodiments. For example, in some embodiments, the resulting film can be scraped from a petri dish with a stainless-steel blade, cut into small fragments using a blade, suspended in Iso Propyl Alcohol (IPA), and crushed in a bead mill using stainless steel (or any other suitable material) beads having any suitable size (e.g., with diameter of 3.17-6.35 mm) for any suitable period of time (e.g., for eight to sixteen hours).

At 158, the particle suspension can next be serially filtered to produce one or more desired ranges of particle sizes. This filtering can be performed in any suitable manner to produce any one or more ranges of sizes of particles. For example, in some embodiments, the particle suspension can be serially filtered using polyethylene terephthalate mesh (PET-mesh) cell strainers with pores ranging from 1-40 μm in diameter. An illustration of such filtering is shown in FIGS. 1C1, 1C2, 1C3, and 1C4, each having a scale bar 176 of 100 μm in accordance with some embodiments. As shown in FIG. 1C1, the particle suspension can first be filtered using a 10 μm sieve 172 to produce particles 174 having sizes up to 10 μm in some embodiments. As shown in FIG. 1C2, the remaining particle suspension (i.e., what does not pass the sieve in FIG. 1C1) can next be filtered using a 20 μm sieve 178 to produce particles 180 having sizes between 10 μm and 20 μm in some embodiments. As shown in FIG. 1C3, the remaining particle suspension (i.e., what does not pass the sieve in FIG. 1C2)

can then be filtered using a 30 µm sieve 182 to produce particles 184 having sizes between 20 µm and 30 µm in some embodiments. As shown in FIG. 1C4, the remaining particle suspension (i.e., what does not pass the sieve in FIG. 1C3) can finally be filtered using a 40 µm sieve 186 to produce particles 188 have sizes between 30 µm and 40 µm in some embodiments. Sieves (cell strainers) (e.g., PET-mesh with pore diameters of 10, 20, 30, and 40 µm) can be obtained from PluriSelect USA™ of El Cajon, CA.

Referring back to FIG. 1B, next, at 160, particles in the desired size range(s) can be resuspended in IPA, the suspension can be sonicated, the suspension can be allowed to precipitate after sonication, and excess IPA can be removed after precipitation. The scale bar 160 of FIG. 1B represents 50 µm. Sonication can be performed in any suitable manner and for any suitable duration in some embodiments. For example, in some embodiments, sonication can be performed at 40 kHz for eight to sixteen hours. In some embodiments, further sieving can be performed after sonification to obtain one or more specific particle size(s).

Chitosan (CS)-based polymers can be used to create an ion-conducting scaffolding polymer matrix in some embodiments. In some embodiments, CS is beneficial for this purpose because its ion conductivity (water-uptake) and adhesiveness can be tuned. In some embodiments, CS-based polymers can be used to create an ion-conducting scaffolding polymer matrix in any suitable manner. For example, in some embodiments, CS can be dissolved in 2% v/v acetic acid, filtered using 40 µm cell strainers, and then concentrated via dehydration to 2.5% w/v. A 40% w/v D-sorbitol solution can be prepared with the chitosan stock. PEDOT particles can then be added dropwise into CS-sorbitol under constant stirring to produce a 2.5:1 (unless otherwise specified) PEDOT:CS by weight suspension. The suspension can then be dehydrated to 0.1% w/v of PEDOT in final solution. CS (50-190 kD, 75-85% deacetylated) and D-sorbitol (BioUltra≥99.5%) is available from MilliporeSigma of St. Louis, MO.

The mixed-conducting particles can be combined with the scaffolding polymer matrix to produce the particulate mixed conducting composites. The mixed-conducting particles can be combined with the scaffolding polymer matrix in any suitable manner, such as by mixing them together.

In some embodiments, the particulate mixed conducting composites provide a reliable, flexible mechanical bonding between conformable substrates due to the bio-adhesive properties of chitosan.

In some embodiments, a distinct color contrast between mixed-conducting particles (dark blue) and the scaffolding polymer matrix (light yellow) enables direct optical imaging. In some embodiments, the autofluorescence of CS can additionally or alternatively leveraged for visualization.

Figure 2A:
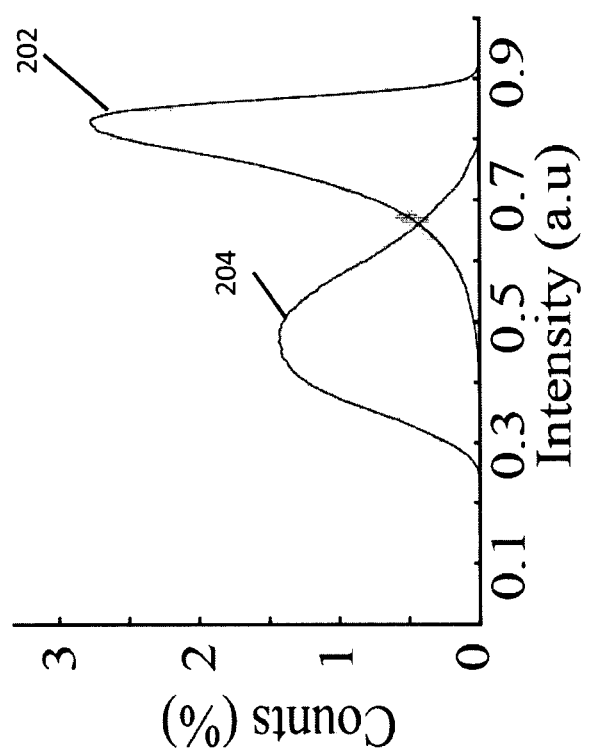
FIG. 2A is an example of a graph showing homogeneity of a distribution of mixed-conducting particles in low density and high density particulate mixed conducting composites in accordance with some embodiments.

To evaluate the homogeneity of the distribution of the mixed-conducting particles in the particulate mixed conducting composites in some embodiments, composites with a low density (ρ) of mixed-conducting particles and a high density (ρ) of mixed-conducting particles were evaluated to produce the graph of FIG. 2A. Optical analysis of same-sized areas blade-coated with each of a low-density composite and a high-density composite revealed that the majority of the pixels in the low-density composite reflected an absence of particles as shown by curve 202 of FIG. 2A, while the distribution of pixel intensity of the high density composite was shifted to the left (darker), indicating the presence of numerous particles, as shown by curve 204 of FIG. 2A. These results suggest that increasing the density of particles results in a homogeneous composite that is uniformly darker when visualized. If particles instead tended to coagulate into focal areas, a multi-peaked distribution would occur as particle density was increased.

Figure 2B:
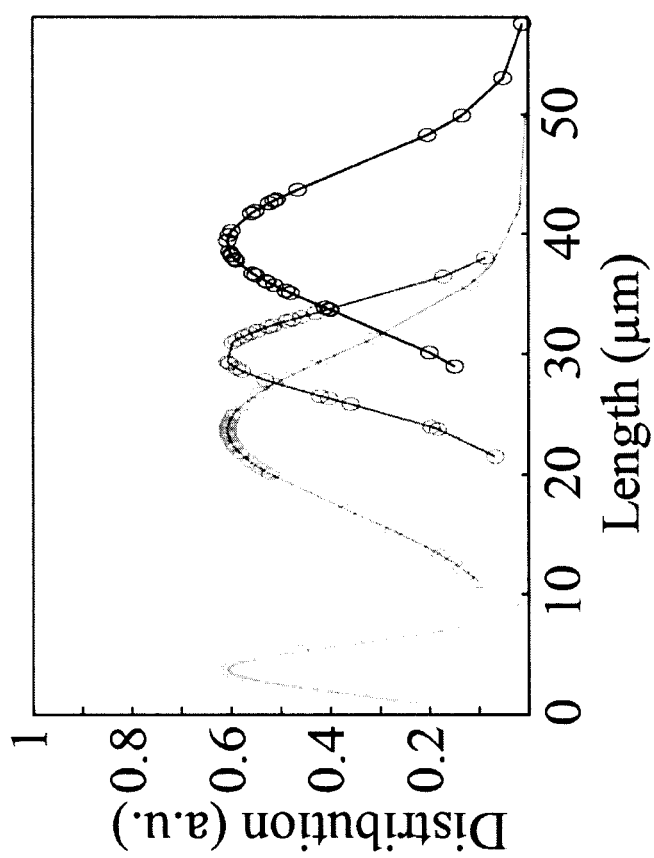
FIG. 2B is an example of a graph showing distributions of different particles sizes of mixed-conducting particles after four different sieving processes in accordance with some embodiments.

Using similar optical methods, it was found that the sieving process described in connection with FIGS. 1C1, 1C2, 1C3, and 1C4 can be highly selective, creating particles ranging from 10-40 µm with narrow size distributions as shown in FIG. 2B.

Figure 2C:
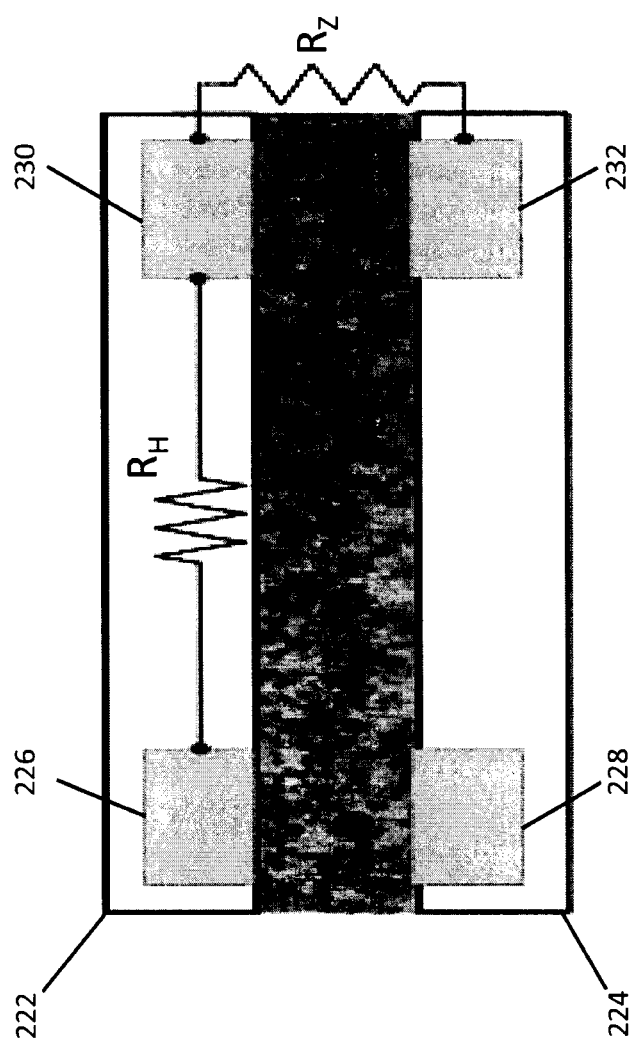
FIG. 2C is an example of a schematic showing a composite sandwiched between two substrates that include multiple horizontally spaced, vertically aligned strips of gold in accordance with some embodiments.
Figure 2D:
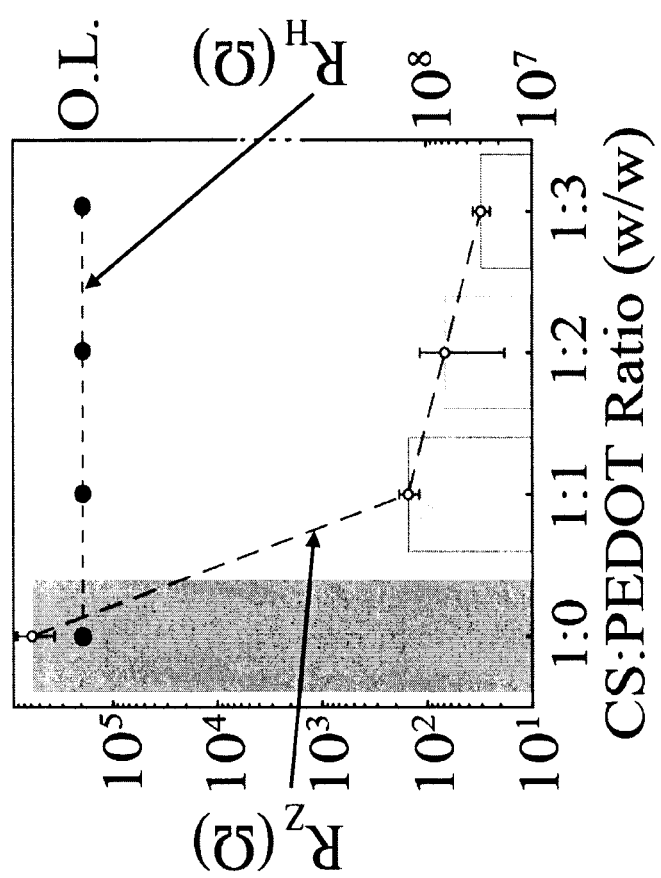
FIG. 2D is an example of graph showing different resistances measured for different composites in accordance with some embodiments.

To characterize the conductivity of the particulate mixed conducting composites in some embodiments, composites with various particle densities, including one without particles (control), were prepared. As shown in FIG. 2C, these composites were sandwiched between two substrates 222 and 224 that included multiple horizontally spaced, vertically aligned strips of gold (Au) (1 mm wide and 100 µm spacing, 100 nm thick) 226, 228, 230, and 232. As shown in FIG. 2D, the composites (bars with 1:1, 1:2, and 1:3; 1:0 is control with no particles) exhibited less than 100 Ω electrical contact resistance between the vertically aligned Au strips. This vertical resistance ($R_Z$) was inversely proportional to particle density, whereas resistance between horizontally spaced Au strips remained high ($R_H > 10^{10}$ Ω).

These features suggest that the particles remain homogenously distributed within the particulate mixed conducting composites when sandwiched between the substrates, without focal coagulation that would cause increased horizontal conduction in some embodiments. Thus, the physical processes used to prepare the particulate mixed conducting composites offers several key advantages in some embodiments: (i) highly controllable generation of particles with specific size and density; (ii) homogeneous distribution of particles within the composite, even after lamination; (iii) preservation of electrical properties of the conducting polymer; (iv) ability to include additives that enhance electrical performance of the composite; (v) solvent-free synthesis, enhancing compatibility with organic materials; and (vi) scalability for a variety of production volumes.

Figure 3A:
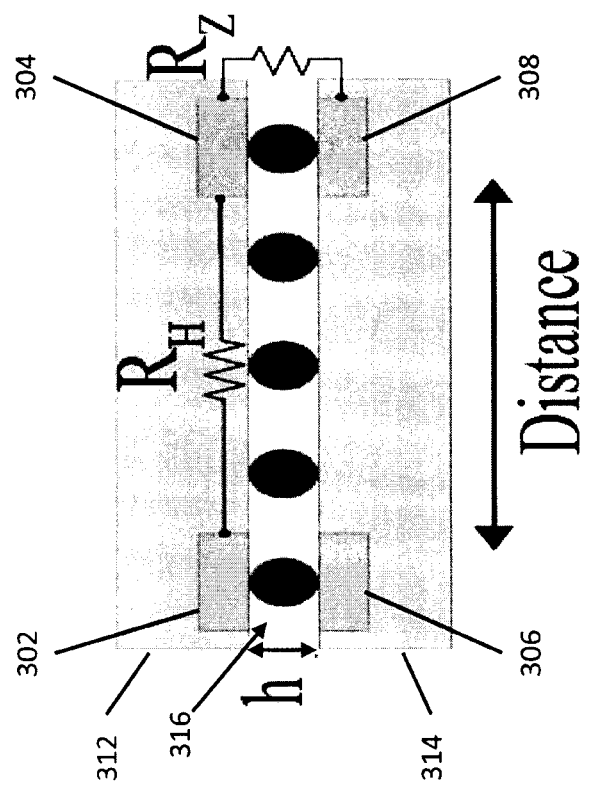
FIG. 3A is an example of another schematic showing a composite sandwiched between two substrates that include multiple horizontally spaced, vertically aligned strips of gold in accordance with some embodiments.
Figure 3B:
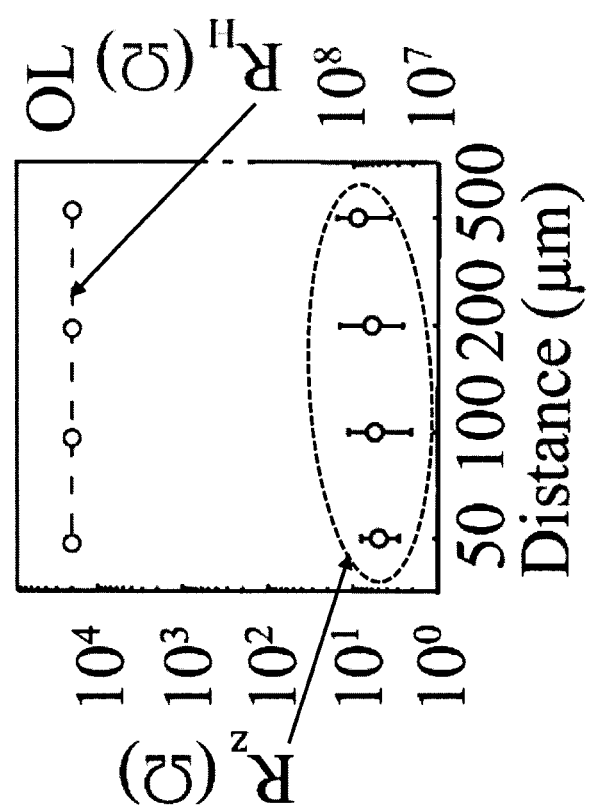
FIG. 3B is an example of a graph showing different resistances measured in composites in accordance with some embodiments.
Figure 3C:
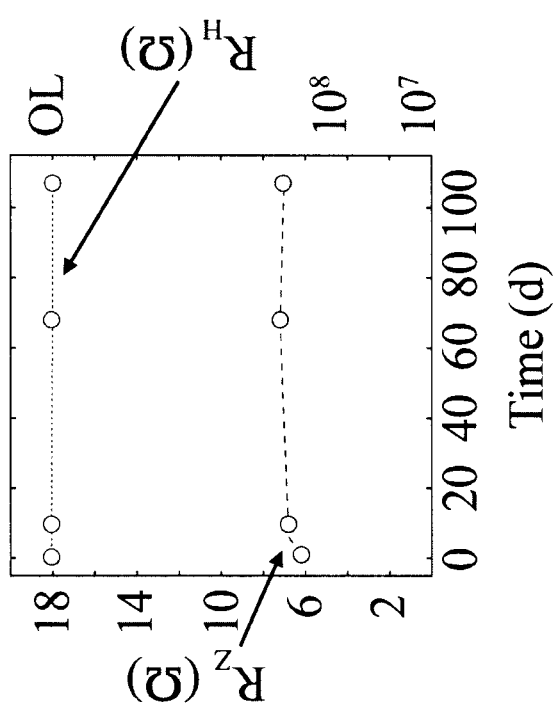
FIG. 3C is an example of a graph showing different resistances measured in composites over time in accordance with some embodiments.

To determine whether a particulate mixed conducting composite has sufficient anisotropy to form high-density vertical interconnects between electronic components without patterning in some embodiments, Au-based electronic pads 302, 304, 306, and 308 were fabricated on rigid ($SiO_2$) and conformable (parylene C) substrates 312 and 314 with geometrically varying inter-electrode spacing as shown in FIG. 3A. A particulate mixed conducting composite 316 was deposited onto bottom substrate 314 using typical solution processible techniques (e.g., spin coating and blade coating) and then covered by top substrate 312. As described above in connection with FIG. 1A3, particulate mixed conducting composite 316 had α and λ less than Distance in FIG. 3A but greater than h in FIG. 3A. Because CS is intrinsically adhesive, the particulate mixed conducting composite established strong mechanical bonds between layers of both rigid and conformable substrates, without requiring elevated temperatures (maximum 70° C.) or application of pressure. Anisotropy (A) of the interface was determined by calculating the ratio ($A = R_H/R_Z$) of the horizontal resistance ($R_H$) between pads 302 and 304 and pads 306 and 308, and vertical resistance ($R_Z$) between pads 302 and 306 and pads 304 and 308. Ensuring that the particulate mixed conducting composite used had a smaller λ than the electrode distance, we were able to achieve anisotropy values of at least $10^6$ as shown in FIG. 3B, and as high as $10^{10}$, at 50 µm resolution. As shown in FIG. 3C for particle size of 40 µm and an electrode pitch of 250 µm, these anisotropy values were consistent for more than 100 days, highlighting the stability of particulate mixed conducting composite's electrical and mechanical bonding.

Figure 3D:
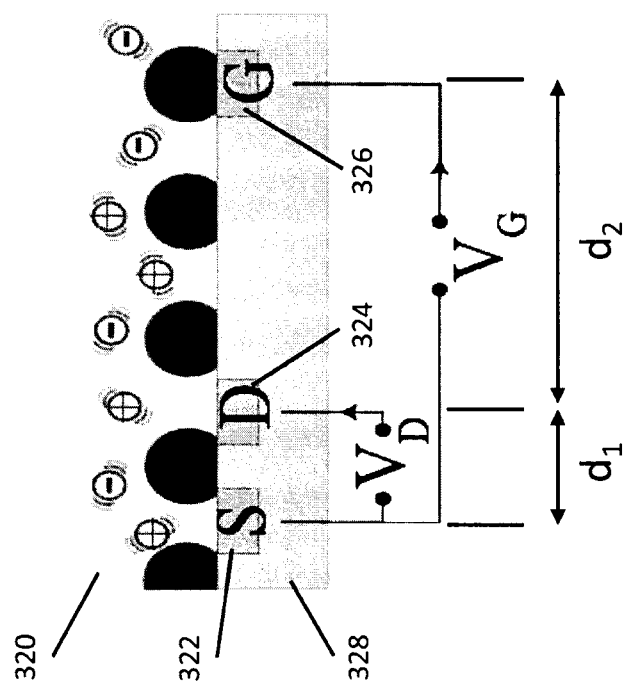
FIG. 3D is an example of a schematic of a particulate mixed conducting composite-based independently gated ionic transistor in accordance with some embodiments.
Figure 3E:
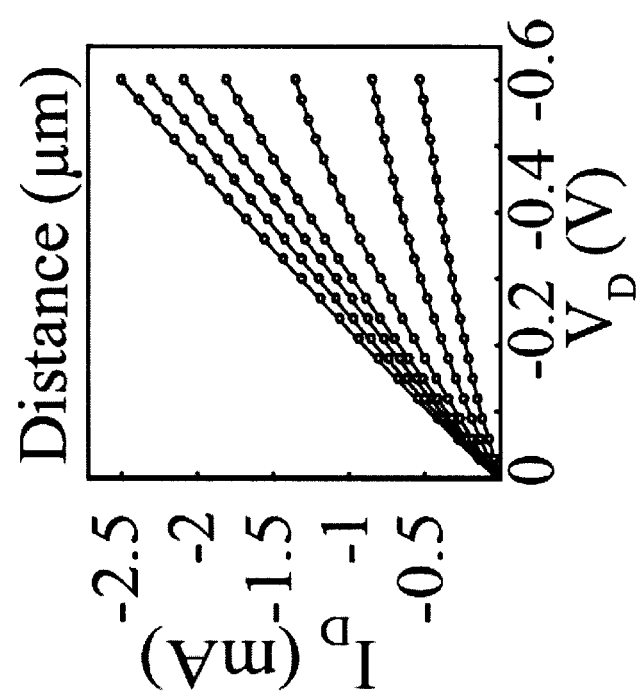
FIG. 3E is an example of graph showing characteristics of a particulate mixed conducting composite-based independently gated ionic transistor in accordance with some embodiments.
Figure 3F:
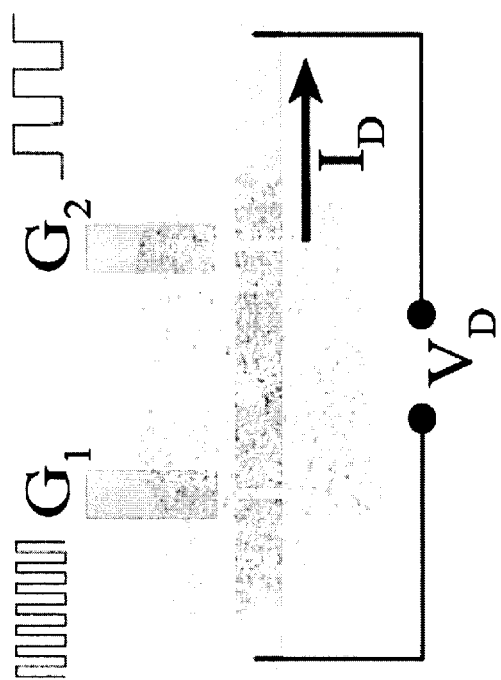
FIG. 3F is an example of a NOR gate constructed using a composite in accordance with some embodiments.
Figure 3G:
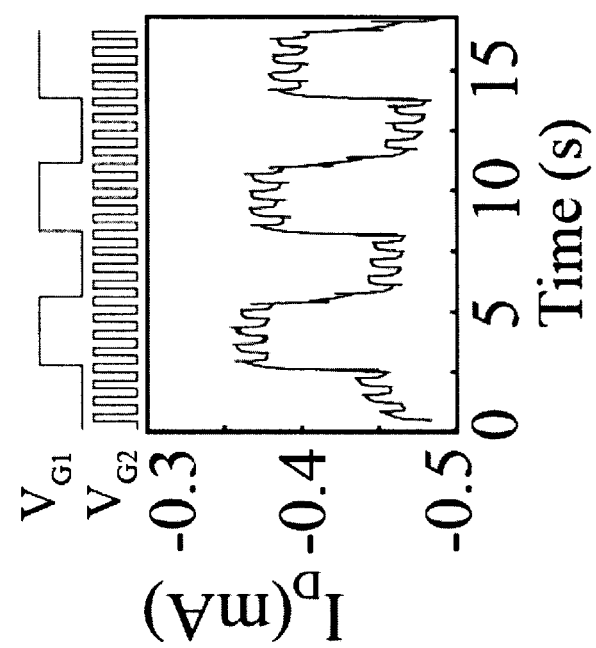
FIG. 3G is an example of a graph showing the behavior of a NOR gate constructed using a composite in accordance with some embodiments.

As shown in FIG. 3D, particulate mixed conducting composite-based independently gated ionic transistors were fabricated by blade-coating particulate mixed conducting composite 320 onto three Au-based pads 322, 324, and 326 (representing a source, a drain, and a gate, respectively) embedded in a substrate 328. As described above in connection with FIG. 1A3, particulate mixed conducting composite 320 had both $\alpha$ and $\lambda$ between $d_1$ and $d_2$. This configuration functioned as a depletion-mode, high-transconductance, individually addressable organic electrochemical transistor. Application of positive gate voltage ($V_G$) across Au pads 322 and 326 directed cations of the ion-conducting scaffolding polymer matrix into the bridging mixed-conducting particles of the channel, resulting in dedoping. The electrical characteristics of the transistor are shown in FIG. 3E. The independent gating of these devices has been used to create logic circuits with series and parallel connectivity between transistor terminals. For example, a NOR gate, as shown in FIG. 3F, has been implemented in which $G_1$ and $G_2$ are the inputs. As shown in FIG. 3G, this particulate mixed conducting composite-based transistors performed the appropriate digital logic. Therefore, in some embodiments, particulate mixed conducting composite can be used to produce independent transistors that maintain the properties of their constituent conducting polymer without requiring any channel patterning.

Figure 3H:
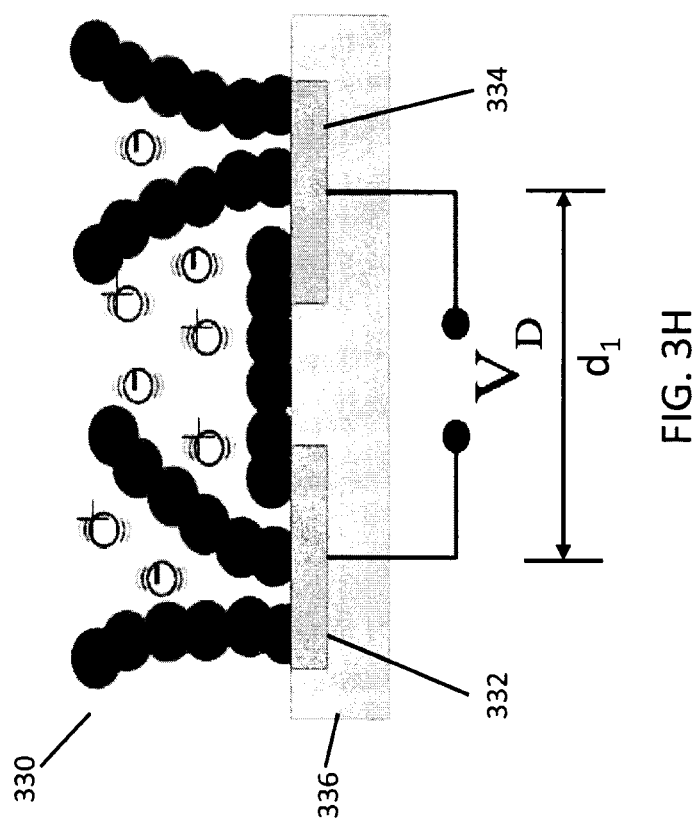
FIG. 3H is an example of a diode constructed using a composite in accordance with some embodiments.
Figure 3I:
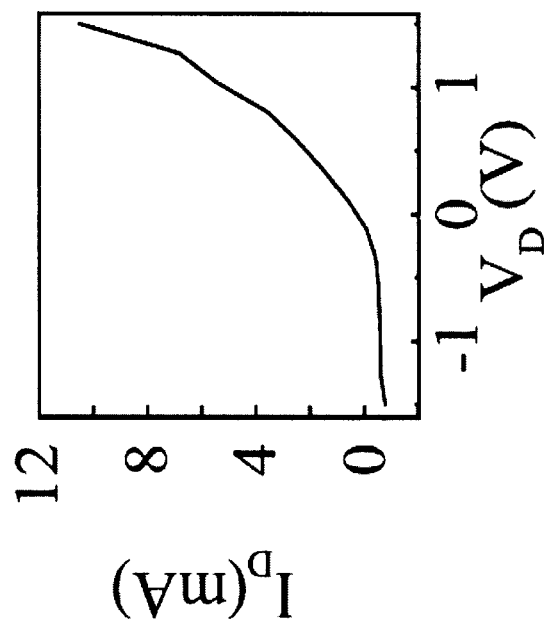
FIG. 3I is an example of a graph showing the behavior of a diode constructed using a composite in accordance with some embodiments.

To determine whether the particulate mixed conducting composite can operate as a diode, as shown in FIG. 3H, particulate mixed conducting composite 330 with appropriate $\alpha$ and $\rho$ was coated onto two Au-based pads 332 and 334 embedded in a substrate 336 and a voltage $V_D$ was applied between the terminals. As described above in connection with FIG. 1A3, particulate mixed conducting composite 330 had $\alpha$ substantially less than $d_1$ of FIG. 3H and $\lambda$ approximately equal to $d_1$ of FIG. 3H. The application of voltage resulted in both (i) electronic current through the bridging particles of the terminals, and (ii) ionic current between omnidirectional particles. As the voltage increased, cations dedoped the bridging particles and lowered the charge carrier density, generating a non-linear voltage-current relationship characteristic of a diode as shown in FIG. 3I.

In some embodiments, the characteristics of the particulate mixed conducting composites enable high spatiotemporal resolution, biocompatible multi-channel electrical contact between soft and hard electronic device components with a facile fabrication process that is adaptable to a wide range of materials. Conformable (parylene C) and flexible (PEN) high-density neural interface devices for integration with flexible (PET) and rigid (FR4) neural acquisition electronic circuits can be fabricated in some embodiments. For example, in some embodiments, a particulate mixed conducting composite can be applied to the back-end of the probe using a blade-coater. The particulate mixed conducting composite will then form an adhesive film (through evaporation of excess water) (e.g., within 120 s at room temperature). A mating board can then be aligned and a mechanical contact established using a manual cotton-based roller with application of pressure (e.g., 0.15 N).

Figure 4A:
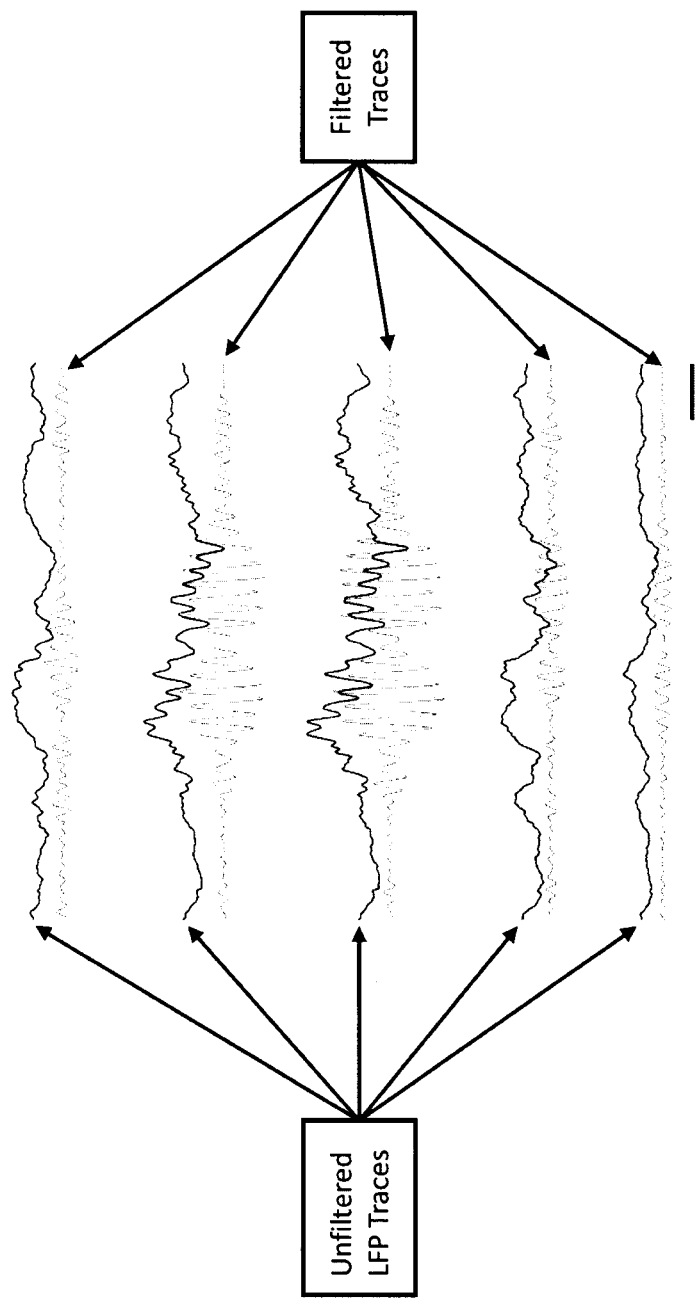
FIG. 4A is an example of a graph showing high gamma oscillations across electrodes of a particulate mixed conducting composite-bonded array placed on a cortical surface of a freely moving rat in accordance with some embodiments.
Figure 4B:
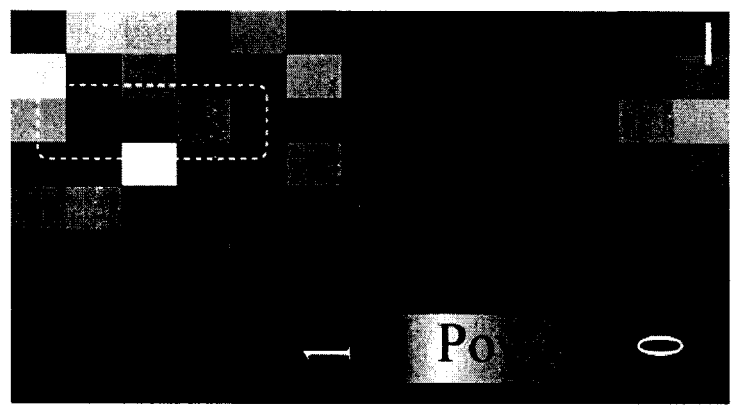
FIG. 4B is an example of a graph showing that trigger-averaged gamma band power can be spatially confined across a particulate mixed conducting composite-bonded array placed on a cortical surface of a freely moving rat in accordance with some embodiments.

To validate the functionality of such particulate mixed conducting composite-bonded devices, some embodiments were used to acquire high spatiotemporal resolution electrophysiological signals in various experimental conditions. Particulate mixed conducting composite-bonded surface electrocorticography (ECoG) arrays (NeuroGrid; 128 channels) and penetrating probes (32 channels) were implanted chronically into freely moving rodents. NeuroGrid recordings demonstrated spatially localized high gamma oscillations as shown in FIGS. 4A and 4B. FIG. 4A shows that, in some embodiments, high gamma oscillations are differentiable across electrodes of a particulate mixed conducting composite-bonded array placed on a cortical surface of a freely moving rat (unfiltered local field potential (LFP) traces and corresponding filtered traces (60-100 Hz)). The scale bar in FIG. 4A is 40 ms. FIG. 4B shows that, in some embodiments, trigger-averaged gamma band power can be spatially confined across a particulate mixed conducting composite-bonded array placed on a cortical surface of a freely moving rat. The scale bar in FIG. 4B is 1 mm.

Figure 4C:
FIG. 4C is an example of a graph showing high fidelity acquisition of characteristic high frequency hippocampal oscillations measured using penetrating probes in accordance with some embodiments.

Insertion of penetrating probes into the dorsal CA1 of the hippocampus allowed high fidelity acquisition of characteristic high frequency hippocampal oscillations as shown in FIG. 4C (ripples, 100-250 Hz) in accordance with some embodiments. FIG. 4C shows sample wide-band traces (0.1 to 20 KHz) superimposed on a heatmap highlighting the instantaneous power in the ripple band (100-150 Hz). The scale bar in FIG. 4C is 50 ms.

Figure 4D:
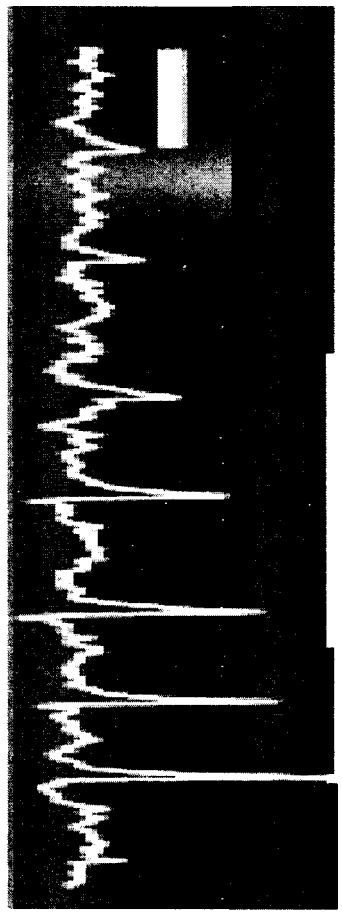
FIG. 4D is an example of a graph showing burst firing of a putative pyramidal cell zoomed in from the location denoted by the white star in FIG. 4C in accordance with some embodiments.

FIG. 4D shows individual action potential waveforms (burst firing of a putative pyramidal cell, zoomed in from the location denoted by the white star of FIG. 4C, 0.1 to 20 KHz). The scale bar in FIG. 4D is 5 ms. Taken together, these results demonstrate that particulate mixed conducting composite bonding can be used to create scalable, multi-channel neural interface devices that are capable of acquiring signals at the spatiotemporal resolution of individual neurons in some embodiments.

The biocompatibility of particulate mixed conducting composites can be used in some embodiments to generate neural interface devices for intra-operative neural recording in human patients undergoing implantation of deep brain stimulation (DBS) electrodes.

In some embodiments, a proximity contact lithography system (Suss MA-6) can be used to pattern Pa-C, Au, Pt, Ti, and PEDOT/PSS films. For example, in some embodiments, first, Pa-C can be deposited using a chemical vapor deposition (SCS Labcoter 2) to a thickness of 2 μm. 3-(trimethoxysilyl) propyl methacrylate can be used as an adhesion promoter and a dilute solution of industrial cleaner (Micro-90) as an anti-adhesion agent. Next, the film can be patterned with a 4.6 μm thick layer of AZ9260 photoresist and dry-etched with a reactive ion etching process (Oxford 80 Plus; 180 W, 50-sccm O2, 3-sccm SF6, 2-sccm CF4 for 18 min). A lift-off process can be used to pattern metal pads and interconnects. AZ nLOF 2020 (chemically amplified negative resist) can be spin-coated on the Pa-C film (5500 rpm), baked at 115° C. for 60 s, exposed using Suss MA-6, and finally developed (AZ developer). With use of an e-beam metal evaporator (Angstrom at $2.10^{-6}$ bars), metallic layers of Ti (10 nm), and Au (150 nm) can be deposited. Lift-off can be performed using 1165 stripper (2 hours). To enhance the conductivity of PEDOT:PSS, a mixture of PEDOT:PSS aqueous dispersion (PH-1000 from H. C. Stark) and ethylene glycol (20:5 ml ratio) can be prepared and mixed with dodecylbenzenesulfonic acid (100 ml per 50 ml) and GOPS (1 w/v %) to adjust surface energy and cross-link, respectively. The resulting dispersion can be spin-coated in two steps with a soft bake in between (120° C., 60 s) at 650 rpm. The films can be subsequently baked at 140° C. for 1 hour and then immersed in deionized water to remove any excess low-molecular weight compounds. The electrodes can be characterized in vitro using phosphate-buffered saline solution. A significantly larger Au plate compared to electrode geometry can serve as the reference electrode for impedance spectroscopy and measurements.

Figure 4E:
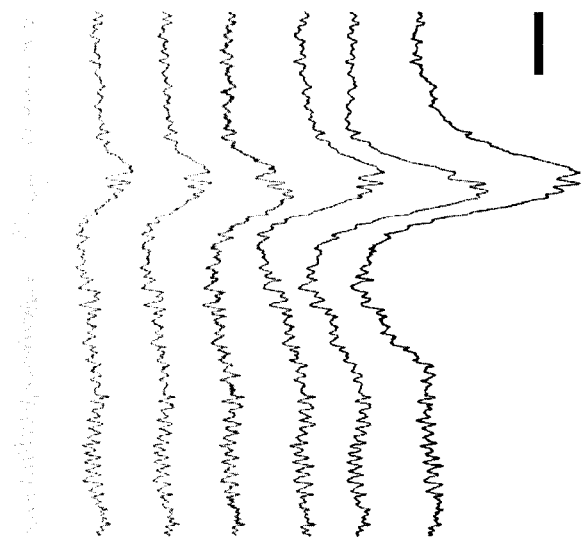
FIG. 4E is an example of a graph showing sample wide-band local field potential (LFP) traces (0.1-1250 Hz) acquired during intra-operative human recording demonstrating spatially diverse activity patterns acquired by a particulate mixed conducting composite-bonded neural probe in accordance with some embodiments.
Figure 4F:
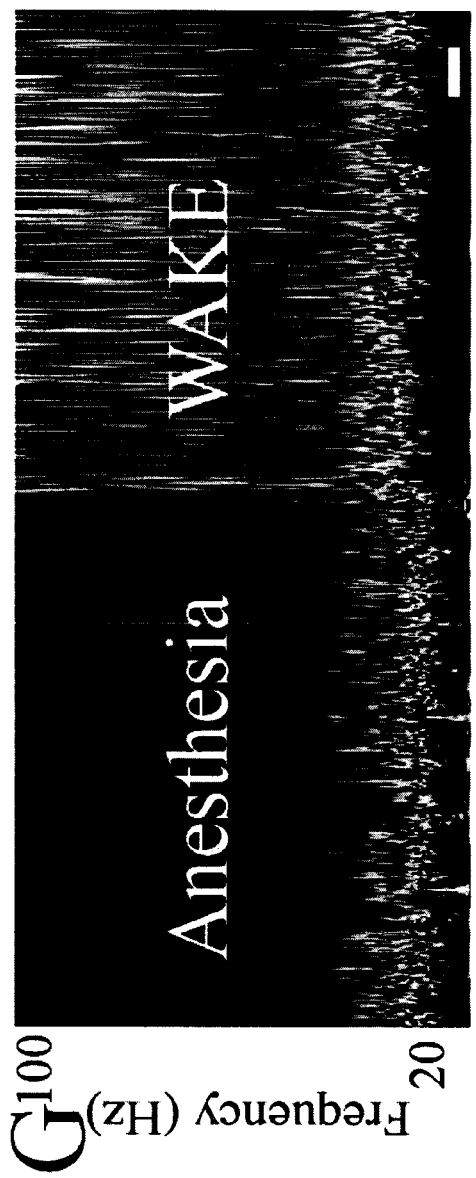
FIG. 4F is an example of a spectrogram of neural data acquired by a particulate mixed conducting composite-bonded neural probe revealing a transition from an anesthetized state to an awake state intra-operatively in accordance with some embodiments.

During a DBS procedure, clinical electrodes can be inserted through a burr hole (which can have any suitable size, e.g., 14 mm diameter) to reach the appropriate subcortical target. In some embodiments, particulate mixed conducting composite-bonded NeuroGrids can be placed within a burr hole and used to acquire spatially resolved, high signal-to-noise-ratio (SNR) neurophysiological data in the intra-operative environment. FIGS. 4E and 4F show data captured in such an embodiment that reveals characteristic signals associated with transition from anesthesia to waking, as well as localized epochs of gamma oscillations. FIG. 4E shows sample wide-band local field potential (LFP) traces (0.1-1250 Hz) acquired during intra-operative human recording demonstrating spatially diverse activity patterns acquired by a particulate mixed conducting composite-bonded neural probe in some embodiments. The scale bar in FIG. 4E is 100 ms. FIG. 4F shows a spectrogram of neural data acquired by a particulate mixed conducting composite-bonded neural probe revealing a transition from an anesthetized state to an awake state intra-operatively. The scale bar in FIG. 4F is 10 s. Thus, particulate mixed conducting composite-bonded neural interface devices can be safely and effectively translated to use in human subjects in some embodiments.

In some embodiments, a particulate mixed conducting composite can be used to interface directly with the human body and enable high spatiotemporal resolution, mechanically stable sensing. For example, as shown in FIG. 4G, in some embodiments, Au-based electrodes 450 coated with a layer of a particulate mixed conducting composite (200 μm diameter) 452 can be applied to a person's skin 454 in some embodiments. More particularly, for example, in some embodiments, electrodes can be placed over a bicep muscle and a wrist of person to acquire EMG and ECG signals. FIG. 4H shows an example of sample traces of a particulate mixed conducting composite-acquired EMG (top) and ECG (bottom) signals measured in accordance with some embodiments. The scale bar in FIG. 4H is 1 s.

Figure 4I:
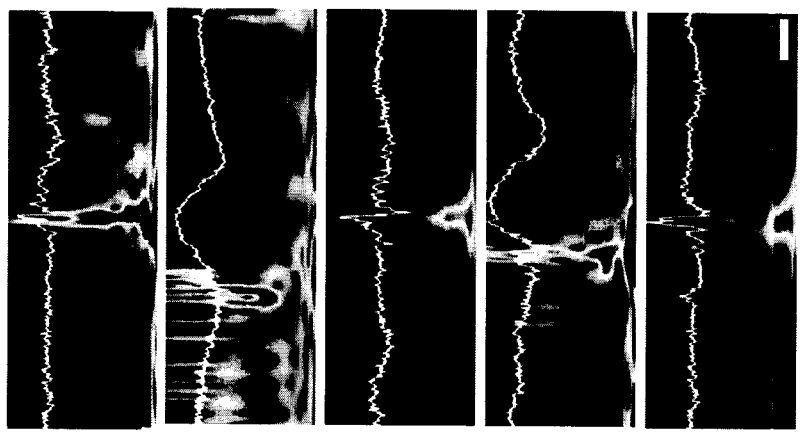
FIG. 4I is an example of five graphs showing differentiable patterns of neural activity across an electrode array during voluntary flexion of each finger on a hand measured in accordance with some embodiments.
Figure 4J:
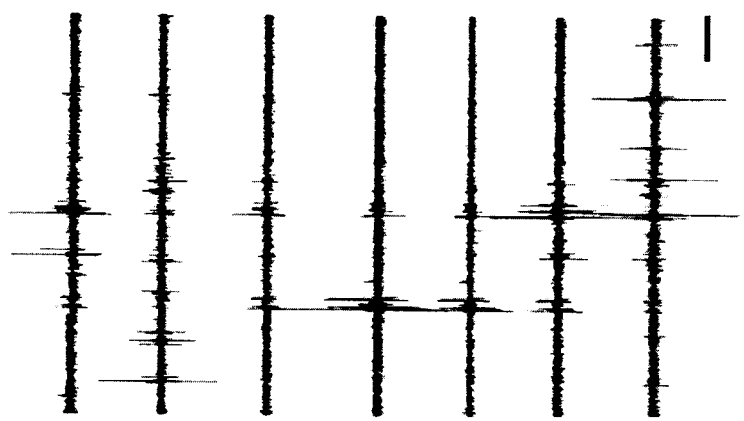
FIG. 4J is an example of a graph showing that multiple adjacent electrodes on an array captured the same action potential in accordance with some embodiments.
Figure 4K:
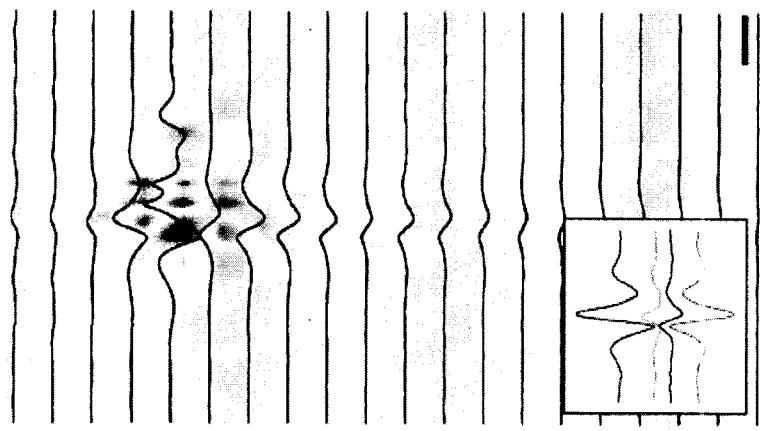
FIG. 4K is an example of a current source density heat map of a sample nerve action potential from FIG. 4J as visualized across adjacent electrodes in accordance with some embodiments.

To evaluate the possibility of higher spatial resolution biopotential acquisition in some embodiments, a conformable array of electrodes (64 channels, 250 μm electrode diameter, 4×7 mm2 effective surface area) was fabricated, a thin layer of particulate mixed conducting composite to a similar surface area of skin over the wrist of a human subject was applied, and the array placed on top. Voluntary flexion of each finger resulted in differentiable patterns of neural activity across the electrode array as shown in the five graphs of FIG. 4I. The scale bar in FIG. 4I is 80 ms. As shown, it was possible to localize independent nerve action potentials with well-defined waveforms and firing rates. As shown in FIG. 4J, multiple adjacent electrodes on the array captured the same action potential with waveforms reflecting the source and propagation of the activity. The scale bar in FIG. 4J is 100 ms. FIG. 4K shows an example of a current source density heat map of a sample nerve action potential from FIG. 4J as visualized across adjacent electrodes and reveals source localization and propagation. The scale bar in FIG. 4K is 5 ms.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A device comprising:
 a composite, comprising:
  particles that are formed from a conducting polymer; and
  an ion conducting scaffolding matrix, wherein the ion conducting scaffolding matrix is phase separated from the particles; and
 three electrodes, wherein: each of the three electrodes is in contact with the composite; a first pair of the three electrodes are on opposite sides of the composite and are a distance h apart; a second pair of the three electrodes are on a same side of the composite and are a distance $d_1$ apart; a particle size of the particles is between h and $d_1$; a mean-free-path of the particles is less than $d_1$; and the composite behaves like an anisotropic conductor.

2. A device comprising:
 a composite, comprising:
  particles that are formed from a conducting polymer; and
  an ion conducting scaffolding matrix, wherein the ion conducting scaffolding matrix is phase separated from the particles; and
 three electrodes, wherein: each of the three electrodes is in contact with the composite; the three electrodes are on a same side of the composite; a first pair of the three electrodes are a distance $d_1$ apart; a second pair of the three electrodes are a distance $d_2$ apart, where $d_2$ is greater than $d_1$; a particle size of the particles is between $d_1$ and $d_2$; and the composite behaves like an ionic transistor.

3. A device containing the composite of claim 1, further comprising:
 a composite, comprising:
  particles that are formed from a conducting polymer; and
  an ion conducting scaffolding matrix, wherein the ion conducting scaffolding matrix is phase separated from the particles; and
 three electrodes, wherein: each of the three electrodes is in contact with the composite; the three electrodes are on a same side of the composite; a first pair of the three electrodes are a distance $d_1$ apart; a second pair of the three electrodes are a distance $d_2$ apart, where $d_2$ is greater than $d_1$; and the composite behaves like a resistor, and wherein at least one of:
 a particle size of the particles is greater than $d_2$; and a mean-free-path of the particles is less than $d_1$.

4. A device containing the composite of claim 1, further comprising:
 a composite, comprising:
 particles that are formed from a conducting polymer; and
 an ion conducting scaffolding matrix, wherein the ion conducting scaffolding matrix is phase separated from the particles; and
 three electrodes, wherein: each of the three electrodes is in contact with the composite; the three electrodes are on a same side of the composite; a first pair of the three electrodes are a distance $d_1$ apart; a second pair of the three electrodes are a distance $d_2$ apart, where $d_2$ is greater than di; a particle size of the particles is between $d_1$ and $d_2$; a mean-free-path of the particles is between $d_1$ and $d_2$; and the composite behaves like an independently gated ionic transistor.

5. A device containing the composite of claim 1, further comprising:
   a composite, comprising:
      particles that are formed from a conducting polymer; and
      an ion conducting scaffolding matrix, wherein the ion conducting scaffolding matrix is phase separated from the particles; and
   three electrodes, wherein: each of the three electrodes is in contact with the composite; the three electrodes are on a same side of the composite; a first pair of the three electrodes are a distance $d_1$ apart; a second pair of the three electrodes are a distance $d_2$ apart, where $d_2$ is greater than $d_1$; a particle size of the particles is less than $d_1$; a mean-free-path of the particles is between $d_1$ and $d_2$; and the composite behaves like a diode.

6. The device of claim 5, wherein the particles are made from poly (3,4-ethylenedioxythiophene)-poly (styrene-sulfonate).

7. The device of claim 5, wherein the ion conducting scaffolding matrix includes a chitosan (CS)-based polymer.

8. The device of claim 1, wherein the particles are made from poly (3,4-ethylenedioxythiophene)-poly (styrene-sulfonate).

9. The device of claim 1, wherein the ion conducting scaffolding matrix includes a chitosan (CS)-based polymer.

10. The device of claim 2, wherein the particles are made from poly (3,4-ethylenedioxythiophene)-poly (styrene-sulfonate).

11. The device of claim 2, wherein the ion conducting scaffolding matrix includes a chitosan (CS)-based polymer.

12. The device of claim 3, wherein the particles are made from poly (3,4-ethylenedioxythiophene)-poly (styrene-sulfonate).

13. The device of claim 3, wherein the ion conducting scaffolding matrix includes a chitosan (CS)-based polymer.

14. The device of claim 4, wherein the particles are made from poly (3,4-ethylenedioxythiophene)-poly (styrene-sulfonate).

15. The device of claim 4, wherein the ion conducting scaffolding matrix includes a chitosan (CS)-based polymer.

* * * * *